United States Patent
Carter et al.

(10) Patent No.: US 12,138,036 B2
(45) Date of Patent: Nov. 12, 2024

(54) CAPNOMETER

(71) Applicant: CAMBRIDGE RESPIRATORY INNOVATIONS LTD, Cambridge (GB)

(72) Inventors: Julian Charles Carter, Cambridge (GB); Benjamin Jeremy Walsh, Cambridge (GB); John Lawrence Altrip, Cambridge (GB); Nalinkumar Lallubhai Patel, Cambridge (GB); Russell Barr Overend, Cambridge (GB)

(73) Assignee: CAMBRIDGE RESPIRATORY INNOVATIONS LTD, Cambridge (GB)

( * ) Notice: Subject to any disclaimer, the term of this patent is extended or adjusted under 35 U.S.C. 154(b) by 324 days.

(21) Appl. No.: 16/091,888

(22) PCT Filed: Apr. 5, 2017

(86) PCT No.: PCT/GB2017/050952
§ 371 (c)(1),
(2) Date: Oct. 5, 2018

(87) PCT Pub. No.: WO2017/174983
PCT Pub. Date: Oct. 12, 2017

(65) Prior Publication Data
US 2019/0104965 A1    Apr. 11, 2019

(30) Foreign Application Priority Data
Apr. 5, 2016 (GB) ..................... 1605826

(51) Int. Cl.
*A61B 5/083*   (2006.01)
*A61B 5/00*    (2006.01)
(Continued)

(52) U.S. Cl.
CPC .......... *A61B 5/0836* (2013.01); *A61B 5/1171* (2016.02); *A61B 5/1172* (2013.01);
(Continued)

(58) Field of Classification Search
CPC ... A61B 5/0836; A61B 5/1171; A61B 5/7282; A61B 5/1172; A61B 5/4839;
(Continued)

(56) References Cited

U.S. PATENT DOCUMENTS 5,261,415 A  * 11/1993  Dussault ............ G01N 21/3504
73/23.3
6,216,692 B1 *  4/2001  Todokoro ............. A61M 16/08
128/204.23

(Continued)

FOREIGN PATENT DOCUMENTS

EP    2008581 A2    12/2008
GB    1712178 A2    10/2006
(Continued)

OTHER PUBLICATIONS

International Search Report and Written Opinion dated Jul. 17, 2017.
UK Search Report dated Aug. 10, 2016.

*Primary Examiner* — Rene T Towa
*Assistant Examiner* — Justin Xu
(74) *Attorney, Agent, or Firm* — Fresh IP PLC; Clifford D. Hyra; Aubrey Y. Chen

(57) ABSTRACT

We describe a capnometer for analysing respiratory system function of a patient, the capnometer comprising: a memory to store patient data which is specific to said patient; and a signal processor to analyse a $CO_2$ waveform representing a variation over time in a $CO_2$ level of air inhaled and/or exhaled by said patient.

24 Claims, 6 Drawing Sheets

(51) Int. Cl.
  *A61B 5/1171* (2016.01)
  *A61B 5/1172* (2016.01)
  *G06V 40/10* (2022.01)
  *G16H 10/60* (2018.01)
  *G16H 20/10* (2018.01)

(52) U.S. Cl.
  CPC .......... *A61B 5/4833* (2013.01); *A61B 5/4839* (2013.01); *A61B 5/7282* (2013.01); *A61B 5/746* (2013.01); *G06V 40/10* (2022.01); *G16H 10/60* (2018.01); *G16H 20/10* (2018.01); *A61B 2560/0252* (2013.01); *A61B 2560/0257* (2013.01)

(58) Field of Classification Search
  CPC .................. A61B 5/746; A61B 5/4833; A61B 2560/0252; A61B 2560/0257; G16H 10/60; G16H 20/10; G06K 9/00885
  See application file for complete search history.

(56) References Cited

U.S. PATENT DOCUMENTS

| | | | |
|---|---|---|---|
| 2005/0245835 A1* | 11/2005 | Butler | A61B 5/42 600/532 |
| 2007/0191688 A1 | 8/2007 | Lynn | |
| 2008/0009762 A1* | 1/2008 | Hampton | A61B 5/0836 600/532 |
| 2009/0118632 A1 | 5/2009 | Goepp | |
| 2012/0165684 A1* | 6/2012 | Sholder | G16H 15/00 600/483 |
| 2012/0272713 A1 | 11/2012 | Kountotsis et al. | |
| 2013/0041279 A1* | 2/2013 | Heath | A61B 5/725 600/532 |
| 2013/0317837 A1 | 11/2013 | Ballantyne et al. | |
| 2014/0180138 A1 | 6/2014 | Freeman et al. | |
| 2014/0361176 A1* | 12/2014 | Russell | G01N 33/50 250/343 |
| 2014/0378779 A1* | 12/2014 | Freeman | A61B 5/1032 600/301 |
| 2015/0178463 A1* | 6/2015 | Criner | A61B 5/7275 705/2 |
| 2015/0216417 A1* | 8/2015 | Huang | A61B 5/7221 600/476 |
| 2016/0374591 A1* | 12/2016 | Shapir | A61B 5/0836 600/532 |
| 2016/0377596 A1* | 12/2016 | Kusaba | G01N 21/3504 600/532 |
| 2017/0020398 A1* | 1/2017 | Emadzadeh | A61B 5/02438 |

FOREIGN PATENT DOCUMENTS

| | | | |
|---|---|---|---|
| WO | WO1999020332 A1 | 4/1999 | |
| WO | WO2002045566 A2 | 6/2002 | |
| WO | WO2008081449 A2 | 7/2008 | |
| WO | WO2009051829 A1 | 4/2009 | |
| WO | WO2012142608 A2 | 10/2012 | |
| WO | WO2015009792 A1 | 1/2015 | |
| WO | WO-2015066562 A2 * | 5/2015 | ........... A61B 5/0024 |
| WO | WO2015166485 A1 | 11/2015 | |

* cited by examiner

CAPNOMETER

FIELD OF THE INVENTION

This invention generally relates to a capnometer and a system for analysing respiratory system function of a patient, and a method of monitoring patient compliance with a drug-taking regime using a capnometer.

BACKGROUND TO THE INVENTION

There is an unmet clinical need to manage patients with chronic respiratory conditions, such as, but not limited to, asthma, bronchiectasis and chronic obstructive pulmonary disease (COPD).

So far, low-cost solutions for managing this need have failed. For example, spirometry, which has been the most common tool to date of pulmonary function tests, is relatively complex when analysing measurement results, which is further complicated by non-tidal breathing and its variability.

pH diagnostic methods require the use of masks and are only suitable for patients with more acute conditions. These methods are therefore not suitable for everyday life usage.

Clinical studies have demonstrated that capnography may be used to detect changes in respiratory function associated with exacerbations in the most common chronic respiratory diseases. The method requires normal tidal breathing and the obtained data may be transformed into a simple personalised indicator of a respiratory condition.

The concept of using capnometry to monitor the respiratory conditions of a patient is well known; see for example, Gunther Lenz and Wolfram Heipertz, J. of Clinical Monitoring, Vol 7, No 3, July 1991. Capnometers are now routinely available in hospitals to measure $CO_2$ levels and provide information on patients with acute respiratory problems.

The capnometer captures breathing waveforms that provide information on $CO_2$ as a function of the breathing cycle, with a trained operator using this information to assess the patient condition.

However, it is generally known that some patients do not adhere to the instructions of their medical doctor, physician or other advisor with regard to following the instructed treatment dosage and/or treatment regime, and/or following the instructions on the patient information leaflet accompanying a medicine or apparatus.

There is therefore a need for improving capnography.

SUMMARY OF THE INVENTION

According to a first aspect of the present invention, there is therefore provided a capnometer for analysing respiratory system function of a patient, the capnometer comprising: a memory to store patient data which is specific to said patient; and a signal processor to analyse a $CO_2$ waveform representing a variation over time in a $CO_2$ level of air inhaled and/or exhaled by said patient.

Embodiments of the capnometer described herein allow for providing a personalised product which may be used to measure and analyse the breathing of a person and may provide quantitative analysis specific to the patient that may be used directly by patients as well as health workers to take corrective actions.

The capnometer, which may be a portable device, may be integrated with a (compact) signal processor (e.g. a microprocessor) to provide immediate assessment of the respiratory performance of the patient. The device and analysis may be unique to the patient by collecting and storing patient specific data.

Using patient data which is specific to a particular patient, immediate action may be taken based on the analysis of the $CO_2$ waveform, in particular where certain information about the patient using the capnometer may be required in order to determine what action may be taken based on the $CO_2$ waveform analysis.

The capnometer including data may be unique to a patient, and may therefore provide security and ensure integrity of data collection.

In embodiments, the respiratory system of the patient which is analysed comprises one or more of the patient's lung, the trachea, the pharynx, the larynx, the bronchi, the bronchioles, the nose, the mouth, the muscles for respiration, and others.

In a preferred embodiment of the capnometer, the patient data comprises an analysis algorithm, wherein said analysing comprises using the analysis algorithm to analyse the respiratory system function.

The device and analysis may be unique to the patient by collecting and storing analysis algorithms and other patient specific data. The analysis algorithm which is specific to a patient may further enhance security and ensure further integrity of data collection. Furthermore, by providing an analysis algorithm which is specific to the patient, the respiratory system function may be analysed more precisely, in particular since other conditions and variables of the specific patient may be known and may be taken into account when the respiratory system function of the patient is analysed.

In a preferred embodiment of the capnometer, the patient data comprises identification data of the patient. A mechanism may therefore by used such that the capnometer may only be used by a certain authorised patient or patients. A personal identification recognition system may be integrated into the capnometer.

In a further preferred embodiment of the capnometer, the identification data comprises one or more of an identification code, fingerprint data, iris scan data and patient respiratory profile data. Any one or more of those identification means may be used to identify a patient. As outlined above, this may be advantageous insofar that only a certain patient or patients may be able to use the capnometer. The identification code may be, for example a PIN code which the user of the capnometer may need to enter into an input of the capnometer in order to be able to use the capnometer. Additionally or alternatively, the capnometer may comprise a fingerprint scanner and/or an iris scanner. Additionally or alternatively, the capnometer may be configured to determine the identification of a user based on patient respiratory profile data. The user of the capnometer may thereby, for example exhale and inhale through the capnometer such that at least one $CO_2$ waveform may be obtained and stored in the memory.

In a further preferred embodiment of the capnometer, the identification data is received from an external personal device, for example a mobile phone or other device which may be able to transmit data. This may be advantageous as the user of the capnometer may not need to enter any information personally into the device. The connection between the capnometer and the external device may thereby be established, for example by Bluetooth.

Preferably, the identification data is received from the external personal device only if a distance between the capnometer and the external personal device is below a threshold. This may be advantageous as the capnometer may pick up a signal from an external device only within a certain distance between the device and the capnometer, such that only a limited number of signals (or preferably a signal only from the nearest external device) are received and analysed by the signal processor of the capnometer. External devices which are too far away may therefore not be detected or analysed via the signal processor of the capnometer.

In a further preferred embodiment, the capnometer further comprises an identification data input configured to receive the identification data for storage in said memory. This may allow for long-term use of the capnometer by a particular patient or patients as the identification data which is stored in memory may be compared to identification data which may be received via the identification input at a later stage.

In a preferred embodiment, the capnometer can be accessed by the patient only when the identification data matches a first identifier. The signal processor may be configured to compare the identification data received at the identification data input and the first identifier. Only if the identification data matches the first identifier, certain functions of the capnometer may be accessible by the patient. This may, for example, allow for preventing misuse and/or accidental use of the capnometer and/or may provide for identification security.

Preferably, the first identifier is stored in the memory. This may be advantageous as no further external device may be needed to compare the identification data received at the identification data input to the first identifier. The capnometer may therefore provide for all components which may be needed to allow access to the capnometer. Only certain functionalities of the capnometer may be accessible to a specific patient or patients.

Alternatively, the first identifier may be stored external to the capnometer. This may be advantageous as the memory internal to the capnometer may have a limited, relatively small capacity and the memory internal to the capnometer may for example primarily be used to store, for example, respiratory profile data or other data.

In a further preferred embodiment of the capnometer, the signal processor is configured to provide a $CO_2$ level data output defining the $CO_2$ waveform, and wherein the $CO_2$ level data output is stored in the memory or a second memory internal or external to the capnometer for later interrogation. This may be particularly preferable as the respiratory system function may be analysed after it has been recorded using the capnometer. The $CO_2$ level data output may be accessed from the memory internal to the capnometer and analysed, for example by the patient's health carer. Alternatively (or additionally) the $CO_2$ level data output may be accessed from a memory external to the capnometer, to which the $CO_2$ level data output has been sent. This may be advantageous as the memory external to the capnometer may have a larger storage size and may be used to store more data. Additionally, the memory external to the capnometer may be sent to the patient's health carer who can then access the $CO_2$ level data output to analyse a respiratory system function of the patient.

It will be understood that the first memory and the second memory may be integral to a single memory internal to the capnometer.

In a further preferred embodiment of the capnometer, the second memory is automatically re-written periodically after a first period of time. This may be advantageous because the memory may have a limited capacity. This may therefore allow storing only the most recent data and delete older data which may not be needed anymore and/or which may have been analysed, for example by the patient's health carer already.

In a preferred embodiment, the capnometer further comprises a first data communications link for sending and/or receiving data. This may be advantageous as the $CO_2$ waveform which may have been recorded using the capnometer may be sent for example wirelessly to the patient's health carer who may then analyse the respiratory system function of the patient. Preferably, data comprising the $CO_2$ waveform is sent to a first external storage system via said first data communications link. This may be particularly advantageous as this may allow sending the $CO_2$ level data output directly to the first external storage system where it may be accessed immediately and/or later for later interrogation. This may further allow for changing, for example, the drug dose and/or regime. When the medical drug dispensing system is used, the drug type, and/or the dose, and/or the time of dispensing a drug may be controlled by the user's GP or carer, for example after analysis of the waveform and/or analysis of the change of waveform over time, by sending control data to the capnometer.

The external storage system and the above first and/or second memories may be integral to a single memory.

The first data communications link may be used to receive (and/or send) data. This data may comprise, for example, the above-stated first identifier. Furthermore, where the $CO_2$ level data output is analysed external to the capnometer, based on the analysis, instructions regarding a time, and/or a type, and/or a dose of a drug to be dispensed may be received from an external device at the first data communications link. Therefore, the first data communications link may be connected to, for example, the drug dispensing system via the signal processor.

In a further preferred embodiment of the capnometer, the signal processor is configured to analyse the respiratory system function responsive to one or more of: a shape of the waveform, one or more peak heights of the waveform, an amplitude or amplitude variation of the waveform, and a frequency composition of the waveform.

Based on the analysis of these characteristics of the waveform, a respiratory system function of the patient may be tested and analysed regarding, for example, chronic respiratory conditions as those outlined above.

In a further preferred embodiment, the capnometer comprises: an air flow region through which air from said patient's respiratory system passes; an emitter configured to emit light; a detector to detect the emitted light; wherein the emitter and the detector are arranged such that light from the emitter passes through the air flow region to the detector; wherein the signal processor is coupled to the detector to analyse the $CO_2$ waveform.

In a preferred embodiment of the capnometer, the emitter is configured to provide the light at two or more different wavelengths, and the detector is configured to detect the two or more different wavelengths for the signal processor to analyse the respiratory system function. This may be particularly advantageous as the signal which stems from $CO_2$ may at least partially overlap with a signal which may stem from another gas or gas component(s). Emitting and detecting the light at two or more different wavelengths may therefore allow reducing the possibility that the $CO_2$ signal which is to be detected to analyse respiratory system function is disturbed by (a) signal(s) stemming from other gases. A more accurate analysis of patient respiratory system function may therefore be performed.

In a further preferred embodiment of the capnometer, the emitter comprises a mid-IR semiconductor emitter configured to provide the emitted light at a wavelength in the range 3-5 μm; and the detector comprises a mid-IR semiconductor detector. This may be particularly advantageous because these devices may allow for accurate detection of the $CO_2$ signal, in particular as they are configured to emit and detect light at wavelengths at which $CO_2$ absorbs light, and may further be cheap to produce.

Example embodiments of the capnometer will be described below.

It may be preferable to indicate a respiratory system function or a quality of a respiratory system function to the patient (and/or a third person). Therefore, in a preferred embodiment, the capnometer further comprises one or more user indicator devices, wherein, based on the waveform, the user indicator devices indicate a quality of the respiratory system function. These user indicator devices include, but are not limited to, one or more light outputs and/or sound outputs, displays and others. Preferably, the user indicator devices may provide information regarding one or more specific chronic respiratory conditions in addition to a more general respiratory system function.

In a further preferred embodiment, the capnometer further comprises an alarm and/or messenger configured to be triggered dependent on the indication of the quality of the respiratory system function. The alarm and/or message, which may be triggered automatically, may advantageously be sent to the patient's GP or carer.

In a further preferred embodiment, the signal processor is further configured to indicate when a therapeutic intervention is required based on the quality of the respiratory system function, and additionally or optionally based on one or more of the detected and analysed specific chronic respiratory conditions.

It may be preferable to obtain a normalised indication of the respiratory system function which is related to a particular patient only.

Therefore, in a related aspect of the invention, there is provided a capnometer, in particular a capnometer as described in any one or more of the embodiments above, for analysing respiratory system function of a patient, the capnometer comprising a signal processor configured to analyse a $CO_2$ waveform representing a variation over time in a $CO_2$ level of air inhaled and/or exhaled by said patient, wherein said analysis of said respiratory system function is based on a comparison between said waveform and one or more of said waveforms which were obtained previously for said patient.

It will be appreciated that an evaluation of the respiratory system function may be made for a present point in time by comparing the present waveform with one or more waveforms obtained in the past (for example one or more minutes, hours, days, weeks or months etc. in the past). Alternatively or additionally, the respiratory system function at a certain point or period of time in the past may be made by comparing the waveform which was obtained in the past to one or more waveforms obtained even earlier. This may allow for obtaining and analysing information about respiratory system function over an extended period of time. In some embodiments, the previously obtained waveforms may have been obtained during one or more separate uses of the capnometer by the patient. Alternatively, in some embodiments, the comparison may be based on different waveforms which may have been obtained during a single use or session of using the capnometer by the patient during which multiple waveforms may have been detected. It will be understood that previously obtained waveforms may have been stored in memory (internal and/or external to the capnometer) for later retrieval, as will be further described below, in order to make the above-specified comparison.

In some embodiments, one or more parts of the waveforms may be compared, for example the parts where the $CO_2$ waveforms rise, fall and/or level out during the end of the exhaling of air by the patient. In some embodiments, the entire waveforms may be compared.

In a preferred embodiment of the capnometer, the one or more previously obtained waveforms define a metric with a baseline (for example 100%), and the comparing comprises detecting or monitoring a deviation of the waveform from the baseline.

The patient respiratory system function may be analysed even more precisely when the metric is developed specifically to a disease or type of disease the patient may have. Therefore, in a preferred embodiment of the capnometer, the signal processor is further configured to develop the metric with regard to a disease or type of disease of the patient for analysing the patient respiratory system function with regard to this disease or type of disease.

It will be appreciated that the waveform may be analysed with regard to a specific disease or type of disease based on a metric which has been developed based on one or more waveforms obtained previously not only for the patient him-/herself, but additionally or alternatively for one or more different patients.

It may be preferable to adapt the metric over time based on the waveforms which have been obtained over time. Therefore, in a preferred embodiment, the signal processor is further configured to alter the metric over time based on the waveforms. Altering the metric over time may allow for a more precise analysis of the patient respiratory system function which itself may change over time.

In a further related aspect of the present invention, there is provided a capnometer, in particular a capnometer as described in any one or more of the embodiments above, for analysing respiratory system function of a patient, the capnometer comprising a signal processor configured to analyse a $CO_2$ waveform representing a variation over time in a $CO_2$ level of air inhaled and/or exhaled by a user of said capnometer, wherein said signal processor is configured to determine from said waveform one or more of: a first indication of a point in time when a drug has been taken; a second indication of a point in time when a drug should be taken; a third indication of a type of drug which has been taken; a fourth indication of a type of drug which should be taken; a fifth indication of a dose which has been taken; a sixth indication of a dose which should be taken; and a seventh indication that a drug has expired or has been used up.

These indications may in particular be obtained by, for example, analysing one or more of the shape of the waveform, one or more peak heights of the waveform, an amplitude variation of the waveform, and a frequency composition of the waveform. When a drug has been taken, the waveform might change which may then be processed by the signal processor. Similarly, the waveform might change differently for different drugs and/or different doses which may be processed by the signal processor. A change and/or deviation in the waveform may therefore be used to determine one or more of the above-specified indications.

When using a drug, it may be observed that the waveform does not change over time. A lack of change in the waveform may therefore indicate that a drug has been expired as it may not be effective anymore. A non-observation of a change in the waveform may additionally or alternatively indicate that the drug has been used up. The latter may further be determined and indicated by the number of doses which may have been dispensed.

Based on one or more of the above indications, a drug may be released and be provided to the patient. Therefore, in a preferred embodiment, the capnometer further comprises a medical drug dispensing system for controlling a release of a said drug responsive to a said determination. A specific drug and/or a specific dose may be released, preferably at a specific point in time, by the medical drug dispensing system based on one or more of the above indications.

In a preferred embodiment of the capnometer, the medical drug dispensing system is configured to automatically release a said drug and/or control a said type and/or dose and/or point in time of the release of a said drug. In an embodiment, the capnometer is therefore configured to determine, for example, the dose and to indicate to the patient when, for example during the day, the drug and/or dose should be taken. The dose may thereby be determined by analysing the waveform of the $CO_2$ level data output.

In a further preferred embodiment of the capnometer, the signal processor is configured to determine when the drug should be released during a breath cycle. The point in time when the drug should be released may for example be a particular data and/or time of the day, and/or a particular point in time during a breath cycle. The dose to be released during a specific point or period of the breath cycle may thereby be determined by analysing the waveform of the $CO_2$ level data output.

In embodiments, the patient may use the capnometer successively at two or more points in time over a period of, for example a few hours, a few days, a few weeks, a few months, or even longer. As outlined above, by successively using the capnometer, a variation in a condition of the patient respiratory system function may be determined and analysed. Alternatively, changes of the waveform over time may be determined during a single use/session of the capnometer by the patient, i.e. where a plurality of waveforms are detected during a single use of the capnometer by the patient. Therefore, in a preferred embodiment of the capnometer, the signal processor is further configured to determine, from changes in the waveform over time during a single use or session of use of said capnometer by said patient, a variation in a condition of the patient respiratory system function. The plurality of waveforms may comprise a plurality of waveforms which were obtained consecutively during the single use or session of the capnometer. Alternatively, the waveforms may relate to waveforms which were obtained during a single use or session of the capnometer, but the waveforms do not correspond to consecutively obtained waveforms, but rather to waveforms whereby one or more other waveforms are between the waveforms that may be compared.

It may be preferable to correlate an effect of a drug on the patient with a general wellbeing of the patient. This may allow for determining whether and to what extent a drug may have an effect (which may be positive or negative) on the patient.

Therefore, in a preferred embodiment, the capnometer further comprises a wellbeing data input for allowing the patient to input wellbeing data, the wellbeing data describing a health status of the patient. The health status may be correlated to the respiratory system function of the patient.

In addition or as an alternative to the determination of whether and to what extent a drug may have an effect on the patient, the wellbeing data may be used as an input for other analysis described with regard to the embodiments of the capnometer as outlined throughout the specification. For example, the wellbeing data may be used as an input for patient specific data, and/or as an input for identification data (which may require obtaining historical data such that the patient may be identified based on a pattern in the wellbeing data), and/or compliance with a drug taking regime, and/or as an input which allows for determining a correlation between the shape and/or peak height and/or amplitude and/or frequency composition of the waveform, and/or as an input to trigger the alarm and/or messenger, and/or as an input as to when a therapeutic intervention is required, and/or as an input to define and/or modify the metric, and/or as an input for one or more of the above specified first to seventh indications, and/or the automatic release of the drug and/or its dose and/or its time (for example the date and time, or when during a breath cycle) of dispensing.

In a further preferred embodiment of the capnometer, the signal processor is further configured to process the wellbeing data in combination with the detector signal to determine an effect of a said drug on the patient.

In a related aspect of the invention, there is provided a capnometer for analysing patient respiratory system function, in particular a capnometer as described in any one or more of the embodiments above, the capnometer comprising a signal processor configured to analyse a $CO_2$ waveform representing a variation over time in a $CO_2$ level of air inhaled and/or exhaled by a user of the capnometer and to provide a $CO_2$ level data output defining the waveform, wherein the signal processor is further configured to use the $CO_2$ level data output to determine compliance data identifying episodes when a drug has or has not been taken, and to determine compliance with a drug taking regime from the compliance data. As some patients may not adhere to the instructions of their medical doctor, physician or other advisor with regard to following the instructed treatment dosage and/or treatment regime, and/or following the instructions on the patient information leaflet accompanying a medicine or apparatus, it may be particularly advantageous to provide the capnometer with features which allow for determining compliance data with a drug taking regime.

In a further related aspect of the present invention, there is provided a capnometer for analysing patient respiratory system function, in particular a capnometer as described in any one or more of the embodiments above, the capnometer comprising a signal processor configured to provide a $CO_2$ level data output defining a waveform representing a variation over time in a $CO_2$ level of air inhaled and/or exhaled by a user of said capnometer, wherein said signal processor is further configured to use said $CO_2$ level data output to determine compliance data identifying episodes when a drug has or has not been taken by said patient, and to determine compliance with a drug taking regime from said compliance data; wherein the determination of the compliance with the drug taking regime comprises one or more of: determining whether the patient uses the capnometer to obtain the $CO_2$ level data output; determining, based on the waveform, whether the patient takes the drug; determining whether the patient takes the drug based on drug use data provided by the patient at a drug use data input of the capnometer; and determining whether the drug has been dispensed from the capnometer, for example by the above-specified medical drug dispensing system.

The patient's health carer may be alerted of a patient self-assessment which may be entered by the patient into the (personal) capnometer.

In a further preferred embodiment, the capnometer comprises a data communications link for sending (and optionally receiving) data, wherein the compliance data is sent to an external storage system via the data communications link.

It will be appreciated that the data communications link and the data communications link described earlier in the description may be integral to a single data communications link.

In a preferred embodiment, the compliance data further identifies a dose which has been taken by the patient. This may be advantageous as it may for example be important to monitor an overdose (and/or underdose) which may have been taken by the patient.

In a further preferred embodiment, the capnometer further comprises an alarm and/or messenger configured to be triggered dependent on the compliance data. This may be particularly useful when the patient has not taken a drug (or has taken a drug at a too low dose), or if he has taken a drug with a too high dose. Preferably, the alarm and/or message may further be sent via the data communications link to an external monitoring system which may be monitored by the patient's carer or GP.

In a preferred embodiment, the capnometer further comprises a flow sensor for measuring a flow of air in an air flow region of the capnometer through which air from the patient's respiratory system passes, and wherein the signal processor is further configured to determine a $CO_2$ flow in the air flow region based on the measured air flow. The flow of $CO_2$ may be used to further analyse the patient's respiratory system function.

In a preferred embodiment of the capnometer, the flow sensor comprises a plurality of pressure sensors. Each pressure sensor may detect a pressure gradient which may be correlated to each other in order to determine the flow or flow rate of air, and therefore of $CO_2$ in the air flow region of the capnometer. It may be advantageous to use pressure sensors to determine the $CO_2$ flow in the air flow region of the capnometer, as the pressure sensor may be used for further analysis of the respiratory system function based on the detected pressure in general, for example as outlined further below.

The waveform of the $CO_2$ level may be different for each patient. The $CO_2$ level data output may therefore be used to identify a person using the capnometer. Therefore, in a preferred embodiment of the capnometer, the signal processor is further configured to determine an identity of the patient from the $CO_2$ level data output.

It may be preferable to further monitor a respiration rate of the patient. The respiration rate may be used to analyse whether the patient may have a chronic respiratory condition or any other condition. Various conditions and diseases may be detected and analysed based on the respiration rate.

Therefore, in a preferred embodiment, the capnometer further comprises a respiration rate system for monitoring a respiration rate of the patient and outputting respiration rate data, and wherein the signal processor is further configured to process the respiration rate data.

In a further preferred embodiment, the capnometer further comprises an alarm and/or messenger configured to be triggered in response to a self-assessment by the patient entered at a wellbeing data input of the capnometer, and wherein the alarm and/or message is sent to the patient's GP or carer via a data communications link. The alarm may be integral to the alarm as outlined above. Additionally or alternatively, the wellbeing data input may be integral to the above-described wellbeing data input. Similarly, additionally or alternatively, the data communications link may be integral to the above-described data communications link of the capnometer.

In a further preferred embodiment, the capnometer further comprises a thermometer for measuring a temperature of air in an air flow region of the capnometer. This may be particularly advantageous since the air temperature may have an effect on the condition of the respiratory system of the patient, for example the patient's lung.

In a further preferred embodiment, the capnometer further comprises an air pressure sensor for measuring an air pressure of air surrounding the capnometer. This may be particularly advantageous as the air pressure may be related to weather and/or altitude conditions, which may have an effect on the analysis of the respiratory system function.

In a further preferred embodiment, the capnometer further comprises a location sensor for determining a location of said capnometer. This may be particularly advantageous since the location of the capnometer, and hence the location where it may be used by the patient, may be correlated with known levels of air pollution and/or pollen at any one time and location, which may affect the respiratory system function and/or the analysis of the respiratory system function. The location sensor may be, for example a GPS sensor.

Embodiments of the capnometer may be incorporated into an inhaler.

Therefore, in a related aspect of the invention, there is provided an inhaler comprising the capnometer as described in any of the embodiments herein.

In a further related aspect of the invention, there is provided a system comprising: the capnometer as described in any one or more of the embodiments above; and an analysis system in communication with the capnometer, wherein the analysis system comprises an analysis system memory to store the patient data; and wherein the analysis system is configured to: (i) modify an analysis algorithm based on the analysis of the $CO_2$ waveform by the signal processor; and/or (ii) modify an indicator setting of an indicator of the capnometer based on the analysis of the $CO_2$ waveform by the signal processor, wherein the indicator indicates a quality of the respiratory system function; and/or (iii) change a dose level of a drug dispensed using the capnometer based on the analysis of the $CO_2$ waveform by the signal processor; wherein the analysis system is further configured to transfer the modified analysis algorithm and/or modified indicator setting and/or changed dose level to the capnometer for storage in the memory of the capnometer.

Embodiments of the system therefore allow for modifying for example a drug release based on an analysis of the patient respiratory system function, and/or modifying the algorithm to, for example, more accurately analyse patient respiratory system function (in the future). Additionally or alternatively, the quality of the respiratory system function may be indicated using an indicator so that the patient is aware of the quality respiratory system function and further action may be taken in response to the indication.

Embodiments may further allow for a two-stage analysis of the respiratory condition. The first stage may be performed on the capnometer with the data and algorithm stored locally; the second stage may be a more detailed analysis that may be performed for example on a larger data set which may additionally or alternative include other patient data using higher level of computing resources and more advanced algorithms. The detailed analysis may be used to modify the patient specific algorithms, which may be securely transferred to the patient's capnometer, for example via a data communications link.

In a preferred embodiment of the system, data stored in the memory of the analysis system further comprises patient data specific to further patients, and wherein the modification of the analysis algorithm and/or modification of the indicator setting and/or change of the dose level are further dependent from the patient data specific to the further patients. This may be particularly advantageous because certain patterns in the $CO_2$ waveform and/or the respiratory system function may have for example been detected previously in other patients. This information may be used for the current patient in an advantageous manner in order to, for example, change the dosage of a drug, and/or change the analysis algorithm and/or modify the indicator setting(s), in particular as a certain response of the present patient to, for example, a dosage change may be predicted based on patient data of other patients obtained previously.

Using the data communications link of the capnometer, as outlined above, the patient's GP or carer may be alerted if the patient does not adhere to a drug taking regime. The alarm and/or message may be triggered if the patient does not use the capnometer to assess his/her condition, and/or if the patient does not use the drug as determined by the capnometer waveform, and/or if the patient does not use the drug as determined by the patient not entering the drug use into a drug use data input of the capnometer or inhaler, and/or if no drug is dispensed from the combined capnometer/inhaler.

In a related aspect of the invention, there is provided a method of monitoring patient compliance with a drug-taking regime, the method comprising: monitoring $CO_2$ levels in exhaled breath of the patient with a capnometer, in particular a capnometer as described herein in any one or more of the embodiments; storing data from said monitoring; using the stored data to determine compliance data identifying episodes when said drug has or has not been taken; and determining compliance with said drug taking regime from said compliance data. The assessment may be communicated directly to the patient (and/or the patient's carer) by an indicator and/or display on the capnometer (or inhaler). Based on the indicator, the patient may take appropriate action(s), which may include taking medication and/or making contact with medical support for assistance.

In a preferred embodiment of the method, the compliance data further identifies a dose which has been taken. This may be advantageous as it may be indicated to the patient and/or patient's carer that too high or low a dose has been taken.

In a further preferred embodiment, the method further comprises transmitting the compliance data via a data communication link to a memory which is remote from the capnometer. As outlined above, action may then be taken by the patient's carer or GP, in particular if non-compliance with a drug taking regime is observed. The patient or patient's carer may access the data stored on the memory at a later stage for later interrogation.

In yet another preferred embodiment, the method further comprises triggering an alarm and/or message depending on the compliance data. It will be appreciated that the alarm and/or message may be indicated to the patient, and alternatively or additionally to the patient's carer or GP.

In a further preferred embodiment of the method, the determination of the compliance data is responsive to a patient identification code identifying the patient. This may be particularly preferable when the capnometer (or certain functionalities of the capnometer) ought to be accessible only by a particular patient or patients.

BRIEF DESCRIPTION OF THE DRAWINGS

These and other aspects of the invention will now be further described by way of example only, with reference to the accompanying figures, wherein like numerals refer to like parts throughout, and in which.

DETAILED DESCRIPTION OF PREFERRED EMBODIMENTS

Figure 1:
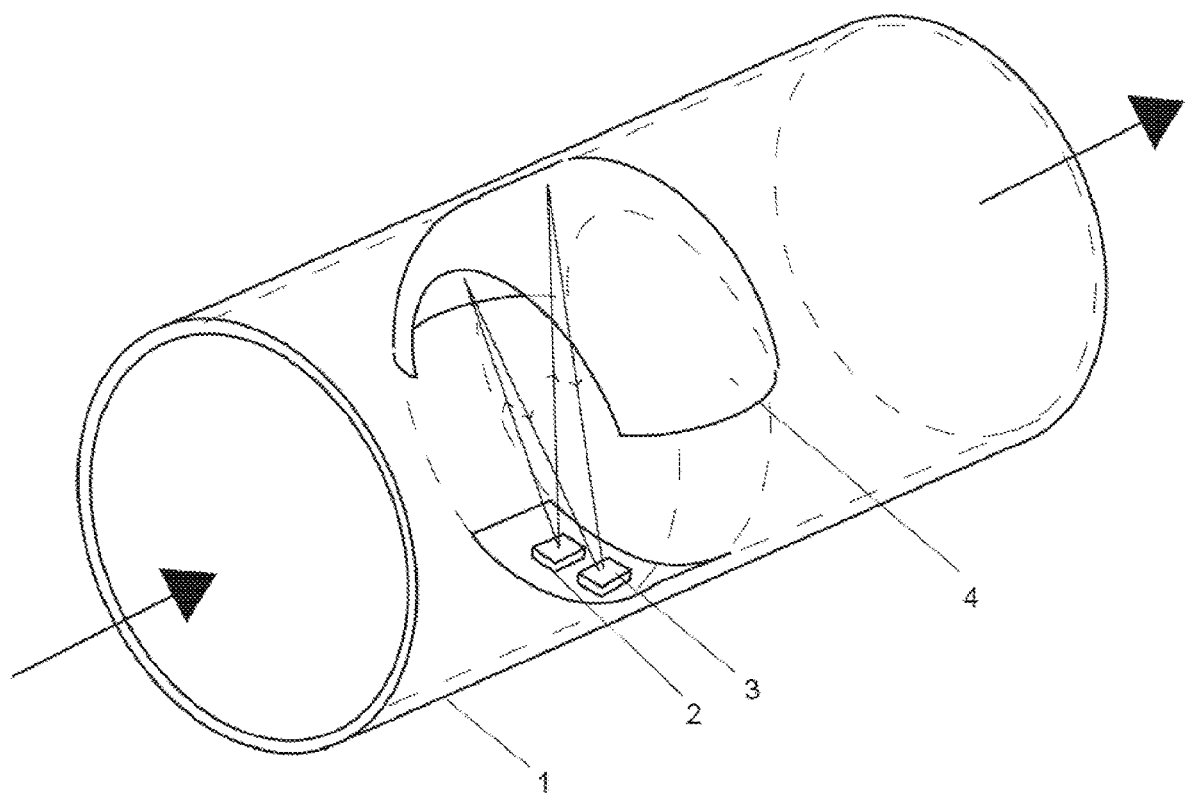
FIG. 1 shows a schematic illustration of components of a capnometer according to embodiments of the present invention.

The capnometer described herein may be used to monitor a $CO_2$ concentration and a $CO_2$ flow to facilitate the diagnosis and therapeutic treatment of patients suffering respiratory diseases, such as, but not limited to, asthma, bronchiectasis and COPD.

Changes in the capnography profile with time may be analysed to assess, for example when to take a therapeutic drug, what drug to take, and what dose is required. Changes in the capnography profile with time, or absence of any changes thereof, may also be used to determine whether a drug is not effective and/or whether a drug has expired.

The capnometer described herein may also be used to optimise delivery of inhaled drugs and demonstrate compliance with a therapeutic regime.

Embodiments of the capnometer described herein may be exploited to provide a signature of a patient's respiratory system condition. The capnometer is small enough to be carried easily and it provides precise personal data of the patient's respiratory system function. A portable, low-cost and easy-to-use capnometer and system is provided with which patients are able to measure their own breathing.

The capnometer is provided with an infra-red (or mid-IR) emitter/detector pair. The emitter/detector pair is in examples described herein configured on a breath tube of the capnometer. The emitter-detector pair is used to determine an instantaneous $CO_2$ concentration.

A flow meter comprising at least two pressure sensors is, in some examples, incorporated into the capnometer allowing for a measurement of the absolute flow of $CO_2$ when a patient breathes through the breath tube.

Electronics surrounding the breath tube is used to record a variation in $CO_2$ flow during patient breathing. This information is stored in a memory, which is internal and/or external to the capnometer.

The capnometer ensures that only the designated patient may be able to use the device. Therefore, in some examples, the capnometer comprises an identification data input configured to receive identification data of the patient. The identification data of the patient comprises in some examples one or more of an identification code, fingerprint data and iris scan data. The identification code is in some examples a PIN code which needs to be entered by the patient, and/or a bar code which needs to be scanned. Alternatively or additionally, near-field communication of the capnometer with an external device, for example, but not limited to, a mobile phone, a key fob or a wrist band device, in the vicinity of the patient may be used to allow only the designated patient to use the capnometer. It will be appreciated that any combination of one or more of the above-specified identification means may be used for a designated patient to access and use the capnometer.

An analysis of the waveform of the $CO_2$ concentration detected with the capnometer allows for a determination that the $CO_2$ variation is that of a particular, designated patient. Therefore, various parameters of the waveform are analysed, for example, but not limited to, an end tidal and a breath rate slope of the waveform. Embodiments of the capnometer can be used as a personal device by a patient without the attendance of a health care professional. As such the device has features to enable reliable measurements which can be made outside the environment of a clinic or hospital.

In one example, the breath tube is covered by ports when not in use to prevent contamination of the optical elements of the device.

In another example, the breath tube contains a fine grid to trap phlegm and other fluids contained in breath from contaminating the optical elements.

Another example of the device allows for analysing the signal level during a breath cycle and determining whether there has been unacceptable contamination of the optical elements, and then indicating to the user that the breath tube needs replacing.

In another example, the device encourages the user to breath consistently by regularly flashing lights and/or beeps at a breath rate suitable for the user.

In another example, the capnometer is integrated with a drug dispensing inhaler device. Such an integrated device can be used to optimise the timing of the delivery of the drug to be at a most effective part of the intake breath.

In another example, the capnometer device contains additional buttons and instructions on an integrated screen so that the user can input when they last took their medication.

In another example, the capnometer records a subjective assessment of how the user is feeling.

In another example, the capnometer device reminds the user to take a measurement and/or take medication.

In another example, the amount of medication is determined by the assessment of the breath profile.

Example Capnometers

We have previously described, in UK patent application GB1421961.2 filed on 10 Dec. 2014 which is incorporated herein by reference in its entirety, embodiments of an improved capnometer. These capnometers exemplify devices which may be used in embodiments of the invention as described herein.

We therefore describe a capnometer for detecting a concentration of a component in a gas, wherein the gas is inhaled and/or exhaled by a patient, the capnometer comprising: an air flow region through which the gas passes to and/or from the patient's respiratory system; a mid-IR semiconductor emitter configured to provide IR light at a wavelength in the range 3-5 µm; a mid-IR semiconductor detector to detect the IR light; a reflector to reflect the IR light emitted by the emitter; wherein the emitter, the detector and the reflector are arranged such that the IR light emitted by the emitter passes through the air flow region via the reflector to the detector.

The capnometer may therefore be used to quantitatively measure the concentration of a particular gas component in a gas mixture using the principle of non-dispersive IR absorption.

The reflecting geometry of the capnometer provides for low cost production and low power consumption. The inventors have realised that rotating elements or beam splitter optics with filters, which are generally employed in a collimated optics geometry, may be made redundant in a capnometer by using the reflecting geometry. The capnometer may therefore be utilised to perform measurements in which an adjacent emitter/detector pair is arranged on one side of a gas sample volume and a reflecting surface is provided on the other side of the gas sample volume.

The reflecting geometry further allows for achieving an appropriate sampling length in order to achieve a good signal-to-noise ratio in the detector at the gas concentration appropriate for respiratory system function measurements, in particular lung function measurements. In the reflecting geometry, the sampling length may be determined by the distance between the emitter and the reflector as well as the distance between the reflector and the detector.

The capnometer may be operated in a non-diverting or substantially non-diverting mode so that high temporal resolution may be achieved when the concentration of the component in the gas is determined.

The capnometer may be implemented in a way which allows the measurement of a gas concentration close to the oro-nasal orifices.

It will be appreciated that a number of configurations may be employed using the reflective geometry.

The emitter can be located at a first location on a first side of the air flow region, the detector can be located at a second location on a second side of the air flow region, wherein the second side is opposite the first side from the air flow region.

In some examples, the reflector is located at a third location on a third side of the air flow region, wherein the third side is adjacent the first and second sides, respectively. The reflector is in some examples further located at a fourth location on a fourth side of the air flow region, wherein the fourth side is opposite the third side from the air flow region. This allows increasing the signal detected by the detector to improve the signal-to-noise ratio.

Alternatively, in some examples a geometry is used in which the emitter is located at a first location on a first side of the air flow region, wherein the detector is located at a second location on a second side of the air flow region, wherein the first side is adjacent the second side, wherein the reflector is located at a third location on a third side of the air flow region, and wherein the third side is opposite the first side or opposite the second side.

It will be understood that a variety of configurations may be exploited in the reflective geometry of the capnometer. The relative locations of emitter, detector and reflector, and/or the shape of the reflector may be modified in order to ensure that IR light emitted by the emitter passes through the air flow region via the reflector to the detector.

In some examples, the capnometer further comprises a breath tube, wherein the breath tube defines a channel between the emitter/detector and the reflector for the air flow region. In some examples, the breath tube is removable from the capnometer. This may be particularly useful since exchanging the breath tube after use may allow for minimising any contamination on the breath tube which could have an undesired impact on the measurements of the gas concentration.

In some example capnometers which use a breath tube, the emitter, the detector and the reflector are mounted in the breath tube. Where the breath tube is removable from the capnometer, exchanging the breath tube with emitter, detector and reflector may allow for minimising any contamination on the emitter, detector and reflector.

In some examples, the capnometer further comprises an optical layer between the emitter and the reflector and/or between the detector and the reflector for improving a collection efficiency of the IR light emitted by the emitter onto the detector. In some examples, this optical layer comprises silicon. Other materials suitable for the optical layer will be known to those skilled in the art, and include, but are not limited to ZnS, ZnSe, Ge, chalocogenide glasses and certain polymers. In some examples where emitter and detector are arranged on the same side of the air flow region, the optical layer is a single layer, or two separate layers between emitter/reflector and detector/reflector, respectively.

In some examples, the emitter and the detector are located external to the breath tube, and the breath tube comprises a mid-IR transmissive portion, wherein the mid-IR transmissive portion is aligned with the emitter and the detector to allow mid-IR light to pass therethrough into and out of the breath tube. In some examples, the mid-IR transmissive portion comprises a separate window. It will be understood that if no separate window is exploited, the breath tube may be mid-IR transmissive at the portion which is aligned with the emitter and the detector. Where the mid-IR transmissive portion comprises a separate window, in some examples, the capnometer further comprises a seal arranged between the breath tube and the separate window. In some examples, the seal is suitable for preventing air surrounding the capnometer from penetrating into the air flow region where the gas is sampled.

In some examples, the mid-IR transmissive portion comprises an anti-reflection coating and/or an anti-fog coating. This increases a collection efficiency of IR light emitted by the emitter onto the detector, and can therefore improve the signal-to-noise ratio as the coatings reduce scattering of IR light on the mid-IR transmissive portion. Alternatively, or additionally, in some examples, the capnometer further comprises a heater for heating the mid-IR transmissive portion. In this way, water condensation on the mid-IR transmissive portion can be prevented in order to increase the collection efficiency and hence the signal-to-noise ratio.

In addition to the mid-IR transmissive portion, in some examples, the capnometer further comprises an optical layer between the emitter and the reflector and/or between the detector and the reflector for improving a collection efficiency of the IR light emitted by the emitter onto the detector. In some examples where emitter and detector are arranged on the same side of the air flow region, the optical layer is a single layer, or two separate layers between emitter/reflector and detector/reflector, respectively. In some examples, the optical layer comprises an anti-reflection coating and/or an anti-fog coating. In some examples, the capnometer further comprises a second heater for heating the optical layer in order to avoid water condensation on the surface of the optical layer. In some examples, the first heater and second heater are integral to a single heater. Furthermore, the mid-IR transmissive portion and the optical layer are, in some examples, integral to a single feature.

As outlined above, in some examples, the optical layer comprises silicon, ZnS, ZnSe, Ge, chalocogenide glasses, certain polymers, or other materials known to those skilled in the art.

In some example capnometers where the emitter and the detector are external to the breath tube, the reflector is mounted in the breath tube. In some examples, the reflector comprises a coating on an inner surface of the breath tube, in particular an anti-reflection and/or an anti-fog coating.

It will be understood that a preferable type of coatings (anti-reflection coating and anti-fog coating) may be determined dependent on the specific materials used for optical layer, reflector, mid-IR transmissive window and other components which may be in contact with the sampling gas.

In some examples, the breath tube comprises one or more alignment features for enabling the arrangement of the reflector with the emitter and the detector. Hence, these alignment features may improve a signal-to-noise ratio of the measurements taken with the capnometer. In some examples, the one or more alignment features comprise alignment pins.

Alternatively, in some examples of the capnometer, the reflector is located external to the breath tube, and the breath tube comprises a second mid-IR transmissive portion, wherein the second mid-IR transmissive portion is aligned with the reflector to allow mid-IR light to pass therethrough into and out of the breath tube.

In some examples of the capnometer, the emitter is configured to provide the IR light at two or more different wavelengths in the range 3-5 µm, and the detector is configured to detect the two or more different wavelengths for the signal processor. These capnometers are particularly suitable for detecting different gases with different absorption peaks or generally different absorption spectra.

In some example capnometers, the reflector is mounted on an inner surface of the breath tube. In some examples, the reflector is integral to the breath tube or integral to a body of the capnometer. Alternatively, in some examples, the capnometer further comprises a reflector mounting for supporting the reflector.

In some examples, the capnometer further comprises a memory to store the level data output. This allows for analysing the gas concentration measured with the capnometer at a later stage.

In some examples, the gas component to be detected in the gas mixture is $CO_2$.

In some examples of the capnometer, the emitter comprises a III-V mid-IR semiconductor emitter.

In some examples of the capnometer, the detector comprises a III-V mid-IR semiconductor detector.

It will be appreciated that the type of emitter and detector may be determined by the gas and/or gas component to be sampled.

In some examples of the capnometer, the reflector comprises a reflective metal film coated with an organic layer. In some examples, the organic layer comprises an anti-reflection coating and/or an anti-fog coating, in particular where the reflector is arranged on an inner surface of the breath tube. In some examples, alternatively or additionally, a heater, e.g. one of the heaters specified above, is provided in the capnometer for heating the organic layer to prevent water condensation on a surface of the organic layer.

It will be important to obtain a sufficient temporal resolution of the measurements to allow the signal to convey enough information about a perfusion and a ventilation of the respiratory system, in particular lungs of a patient. The sample width may be reduced using cut down optics and/or a breath tube design to accelerate gas through the sampling area. Therefore, in some examples of the capnometer, the air flow region has a cross-sectional area which is reduced where the IR light passes through the air flow region.

The capnometer can be used in combination with a medical device, wherein the capnometer further comprises blocking means to inhibit air surrounding the capnometer from flowing into the medical device.

In some examples of the capnometer, the emitter comprises a plurality of emitters, wherein each of the plurality of emitters emits light centred at a different, respective wavelength. This allows different gases with different absorption spectra to be sampled with the capnometer. Furthermore, this capnometer allows for calibrating the device and/or determining when a measurement of a gas concentration is void, as will be further described below.

In some examples, the detector comprises a plurality of detectors, wherein each of the plurality of detectors detects light at a different, respective range of wavelengths.

The design of the optical path is to ensure a good collection efficiency of the optical system, comprising emitter and detector, employed in the capnometer. The use of materials with low absorption at wavelengths where the component absorbs light (e.g. 4.26 μm for $CO_2$) may be preferable. Moreover, in some examples, a high reflective surface of the reflector is provided by, e.g. Au deposited by physical vapour deposition or electrochemical deposition.

We further describe a method of determining when a measurement of a $CO_2$ level in a gas exhaled by a patient in an inspiration/expiration cycle through a capnometer is void, the method comprising: measuring a $CO_2$ level in the gas during the inspiration using the capnometer; and determining that the measurement of the $CO_2$ level in the gas during the expiration is void when the measured $CO_2$ level in the gas during the inspiration is outside a first range of $CO_2$ levels.

Examples of the capnometer described herein may be used to implement this method.

In some examples, the method further comprises determining a corrected $CO_2$ level in the gas during the expiration when the measurement has been determined to be void. Determining a corrected $CO_2$ level in the gas during the expiration is achieved, in some examples, by correcting a signal detected by the detector and/or correcting for the light signal emitted by the emitter. Therefore, in some examples, the correction is applied to one or both of a signal from an emitter of the capnometer and a signal from a detector of the capnometer. Various techniques can be used to determine the corrected $CO_2$ level.

We further describe a method of determining when a measurement of a $CO_2$ level in a gas inhaled and/or exhaled by a patient in an inspiration/expiration cycle through a capnometer is void, the method comprising: providing the capnometer with a plurality of emitters, wherein each of the plurality of emitters emits light at a different, respective wavelength, wherein each of the different, respective wavelengths is within a detecting wavelength range of a detector of the capnometer; pulsing the plurality of emitters during a said inspiration and/or during a said expiration such that the light of each of the plurality of emitters is detected by the detector at a different, respective point in time; determining that the measurement is void when a scattering of the light emitted by the plurality of emitters correlates between at least two emitters of the plurality of emitters.

In some examples, one of the plurality of emitters emits light substantially centred at 4.26 μm. In some examples, the method further comprises correcting a signal from the emitter which emits light substantially centred at 4.26 μm when the measurement is void. Alternatively or additionally, in some examples, a signal from the detector is corrected when the measurement is void.

We further describe a method of calibrating a capnometer, the method comprising: providing a capnometer, in particular an example capnometer as described herein, providing a breath tube comprising a gas with a known $CO_2$ level; inserting the breath tube into the capnometer; measuring the $CO_2$ level of the gas in the breath tube using the capnometer; correlating the measured $CO_2$ level to the known $CO_2$ level; and storing the correlation in a memory of the capnometer.

We further describe a method of calibrating a capnometer, the method comprising: providing a capnometer, in particular an example capnometer as described herein, measuring, using the capnometer, a known $CO_2$ level of air surrounding the capnometer; correlating the measured $CO_2$ level to the known $CO_2$ level; and storing the correlation in a memory of the capnometer.

In some examples, the capnometer described herein is combined with and/or incorporated into an inhaler. We therefore describe an inhaler comprising a capnometer as described in any of the examples herein, wherein the capnometer is configured to monitor a $CO_2$ level in air inhaled through or exhaled through the inhaler.

FIG. 1 shows a schematic illustration of components of an example of a capnometer. The device is used to measure the concentration of a gas component in a sample gas flowing across an air flow region interposed between an emitter (2)/detector (3) pair and a reflector (4). In this example, the emitter (2)/detector (3) pair and the reflector (4) are incorporated into a breath tube (1) and are connected to a suitable electronic drive and detecting circuitry (not shown). In some examples, the value of the detector current is proportional to the emitter current and the amount of gas to be sampled in the sampling area.

The emitter (2) and/or the detector (3) of the capnometer are in this example composed of III-V semiconductors. It will be appreciated that materials suitable for emitter (2) and detector (3) will be known to those skilled in the art. In this example, an emitter diode is designed to emit IR radiation centred around 4.26 μm and the detector (3) is a photo-diode which has a peak sensitivity centred around 4.26 μm.

The path length traversed by the IR light emitted by the emitter (2) and detected by the detector (3) via the reflector (4) is chosen such that the attenuation of the signal by absorption by $CO_2$ molecules is such that a change in intensity can be detected by the detector (3) for the concentration range that is appropriate for the gas stream. For human breath, the range of the $CO_2$ concentration varies between the background $CO_2$ level which is inhaled by the human and up to 5% of gas which is exhaled by the human. In this example, the distance traversed by the IR light is approximately 20 mm.

Figure 2:
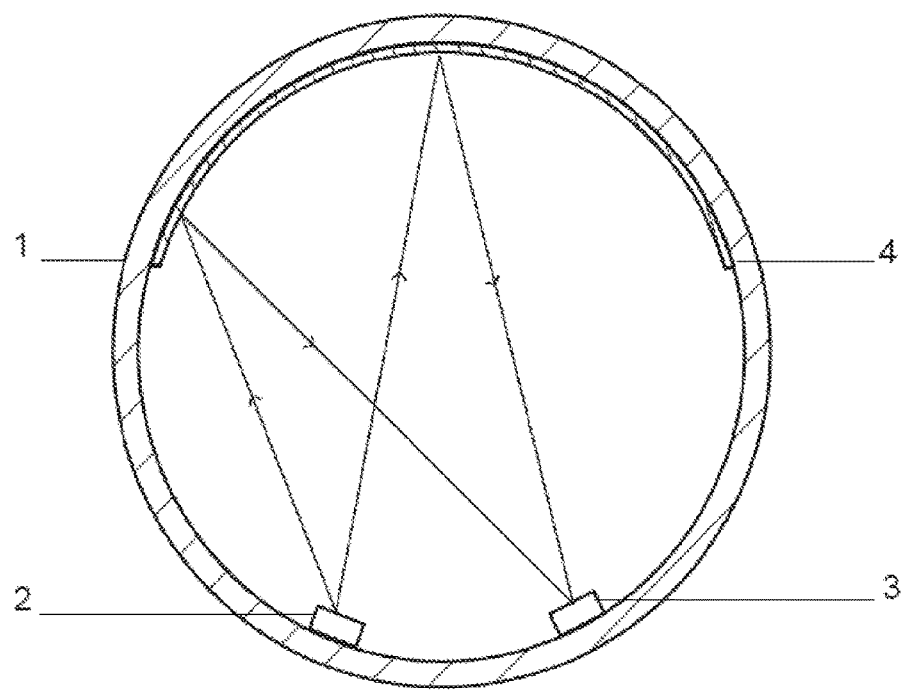
FIG. 2 shows a schematic cross-sectional view of components of a capnometer according to embodiments of the present invention.

As illustrated in the cross-sectional view of FIG. 2, the width of the sampled area is in this example determined by the distance between emitter (2)/reflector (4) and reflector (4)/detector (3). The width of the sampled area is chosen such that the temporal resolution of the system is high enough for the intended application of the device. As outlined above, the air flow region has in some examples a cross-sectional area which is reduced where the IR light passes through the air flow region to increase a time-resolution of the determination of the concentration of the gas component to be determined.

Figure 3:
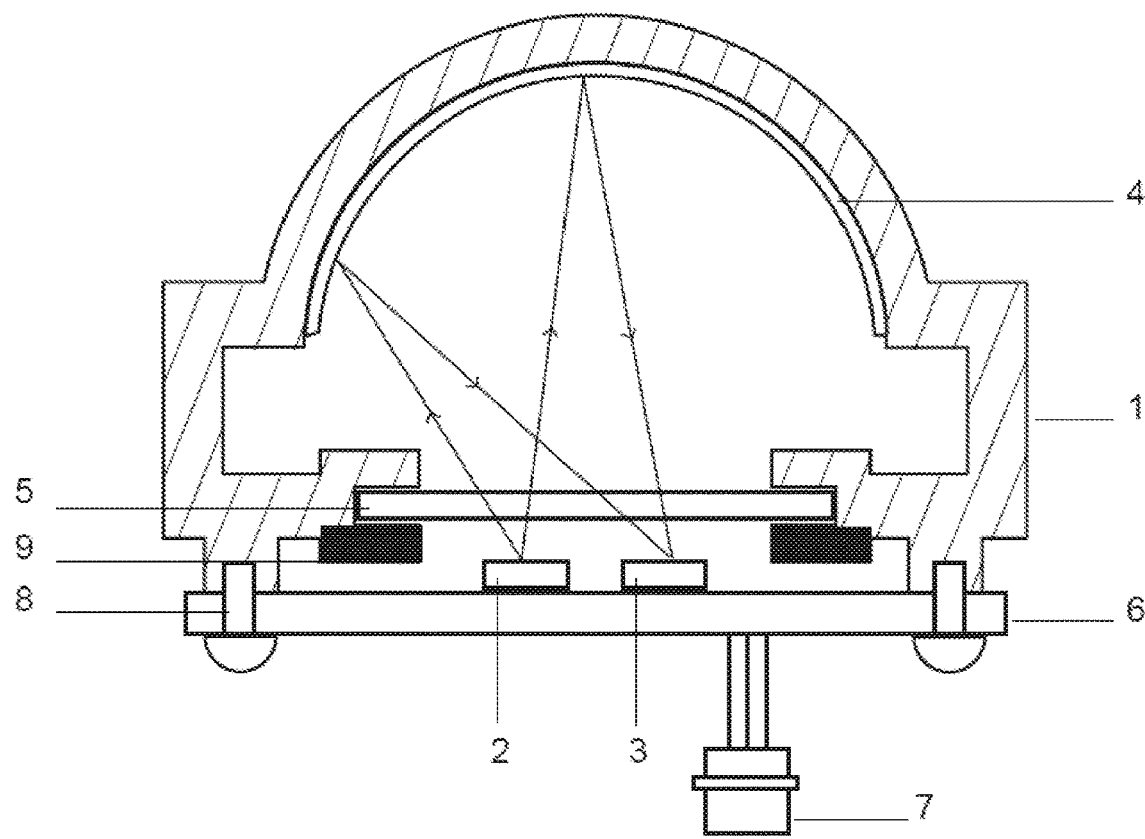
FIG. 3 shows a schematic of a capnometer comprising a silicon optic window.

FIG. 3 shows a schematic illustration of a capnometer comprising a silicon optic window (5). The capnometer is in some examples suitable for a single use. Alternatively, in some examples, the capnometer incorporates a disposable breath tube (1) with a reflector (4) and an optical layer (5) which, in some examples, comprises silicon.

The breath tube (1) is in some examples made from a high-density polymer which has been injection moulded to form a reflector shape. The breath tube (1) is in some examples coated, in this example by evaporation or via an electrochemical method, with a thin metal film which forms a reflector (4) with high reflection efficiency. In this example, the high-density polymer breath tube (1) is coated with a gold film. A variety of materials may be exploited for the breath tube (1) and the reflector (4), such as, but not limited to aluminium and silver.

The breath tube (1) contains in some examples channels which allow a sample gas to be diverted from the air flow region where the sample gas is examined, so that a conductance is achieved which is high enough for the flow to be sampled.

In the example shown in FIG. 3, an optical layer (5) which comprises silicon is provided opposite the reflector (4). The optical layer (5) forms a seal with the breath tube (1). The purpose of the optical layer (5) comprising silicon is both to protect the emitter (2)/detector (3) pair from breath, e.g. to avoid a contamination of the emitter (2)/detector (3) pair, and to increase the collection efficiency of the system by directing more light emitted from the emitter (2) to impinge on the detector (3). Other materials suitable for the optical layer (5) include, but are not limited to ZnS, ZnSe, Ge, chalocogenide glasses and certain polymers. In this example, a gap is provided between the optical layer (5) and the emitter (2)/detector (3) pair. Alternatively, In some examples, the optical layer (5) is in contact with the emitter (2)/detector (3) pair. Furthermore, the optical layer (5) comprises in some examples a plurality of layers between emitter (2) and reflector (4) and/or between detector (3) and reflector (4), respectively.

The capnometer further comprises a seal (9) to prevent gas from the surrounding area from entering the sampling area. In this example, the seal (9) is arranged at two locations where the breath tube (1) and the optical layer (5) connect with each other. The seal (9) can be arranged at one or more locations. In some examples, the seal (9) is arranged on a side facing the air flow region where the breath tube (1) and the optical layer (5) connect, and/or on a side facing away from the air flow region (as shown in FIG. 3).

As outlined above, the optical layer (5) comprises in some examples an anti-reflection coating to minimise losses at interfaces with air.

Surfaces of the reflector (4) and the optical layer (5) which are in contact with the sample gas are in some examples coated with materials which modify the surface energy. Hence, when water condensate from breath condenses on these surfaces, in the case of high surface energy modifiers, the water condensate forms a thin film rather than a droplet or droplets which potentially scatter and therefore reduce the IR radiation impinging on the detector (3). High surface energy materials for coating the surfaces are, for example, hydroxyl and carboxyl containing hydrocarbon thiols. Hydroxyl and carboxyl containing hydrocarbon thiols are particularly suitable for coating a gold surface to form a self-assembled mono-layer. Poly-ethylene oxide or an amine of cyano containing polymers is in some examples deposited on the surfaces of both the reflector (4) and the optical layer (5). In the case of low surface energy modifiers, the water condensate forms droplets that bead up and fall from the window, or in the case of the reflector (4) coat less of the reflector (4) and so have less effect on the signal. Low surface energy materials are, for example fluoro-carbon containing molecules. Fluoro-carbon thiols are particularly suitable for coating a gold surface using a self-assembled mono-layer.

In addition or in place of surface energy modifying materials, the reflector (4) and/or optical layer (5) which are in contact with the sample gas are in some examples heated so that the surface temperature is high enough to prevent condensation on the reflector (4) and/or the optical layer (5).

The distance between the optical layer (5) and the emitter (2)/detector (3) pair is in some examples kept as small as practical in order to minimise any sampling of gas surrounding the breath tube (1). In some examples, this distance is less than 1 cm, less than 1 mm, or even less than 0.1 mm. In this example, this distance is typically less than 0.1 mm.

In this example, a gap is provided between the optical layer (5) and the emitter (2)/detector (3) pair. Alternatively, in some examples, the optical layer (5) is in contact with the emitter (2)/detector (3) pair. Furthermore, the optical layer (5) comprises in some examples a plurality of layers between emitter (2) and reflector (4) and/or between detector (3) and reflector (4), respectively.

The emitter (2)/detector (3) pair are mounted on a printed circuit board (6) which incorporates high precision locating lugs for locating pins (8) that are incorporated into the injection moulded breath tube (1). This allows for a high precision alignment of the emitter (2)/detector (3) pair to the reflector (4) so that high collection efficiency may be achieved.

In some examples, the printed circuit board (6) allows for a connection between the emitter (2)/detector (3) pair and the driving circuit.

An electrical connector (7) is connected to the printed circuit board (6) in order to drive the emitter (2)/detector (3) pair.

In some examples, the system is designed such that the whole assembly can be removed from the driving electronics and body of the capnometer, and can be replaced. Therefore, the breath tube assembly comprising reflector (4), optical layer (5) and emitter (2)/detector (3) printed on the circuit board (6) can be disposed after use of the capnometer.

Figure 4:
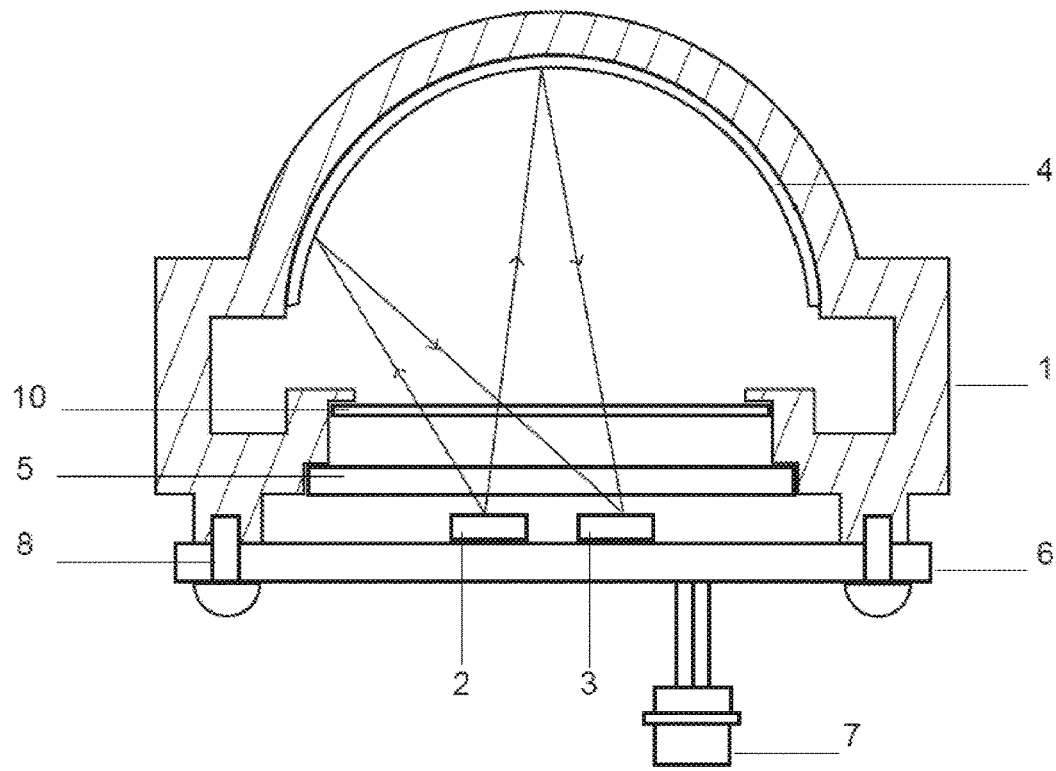
FIG. 4 shows a schematic illustration of a capnometer comprising an IR-transmissive window.

FIG. 4 shows a schematic of a capnometer comprising an IR-transmissive window (10). We note that any references to IR-transmissive of any of the components described herein comprises IR-transparent. The IR-transmissivity of any of the component may be above a pre-defined threshold.

In this example, the device comprises an injection moulded breath tube (1) with a coating to form a reflector (4).

Furthermore, in this example, opposite the reflector (4) there is an opening which is covered by a window (10) which has a low attenuation to IR radiation. Materials for such an IR-transmissive window (10) include, but are not limited to, polyolefins such as polyethylene. The thickness of the window (10) is preferably less than 1 cm, more preferably less than 1 mm, or even more preferably less than 100 μm. In this example, the thickness of the IR-transmissive window (10) is less than 100 μm.

The breath tube (1) with reflector (4) and thin IR-transmissive window (10) incorporates pins (8) which locate with the printed circuit board (6) containing the emitter (2)/detector (3) pair covered with an optical layer (5) comprising silicon. This allows for the breath tube (1) to be removable from the capnometer. In this manner, a lower-cost disposable breath tube (1) is manufactured. Additionally or alternatively, locator pins (8) are in some examples incorporated into the printed circuit board (6).

An electrical connector (7) is connected to the printed circuit board (6) in order to drive the emitter (2)/detector (3) pair.

Figure 5:
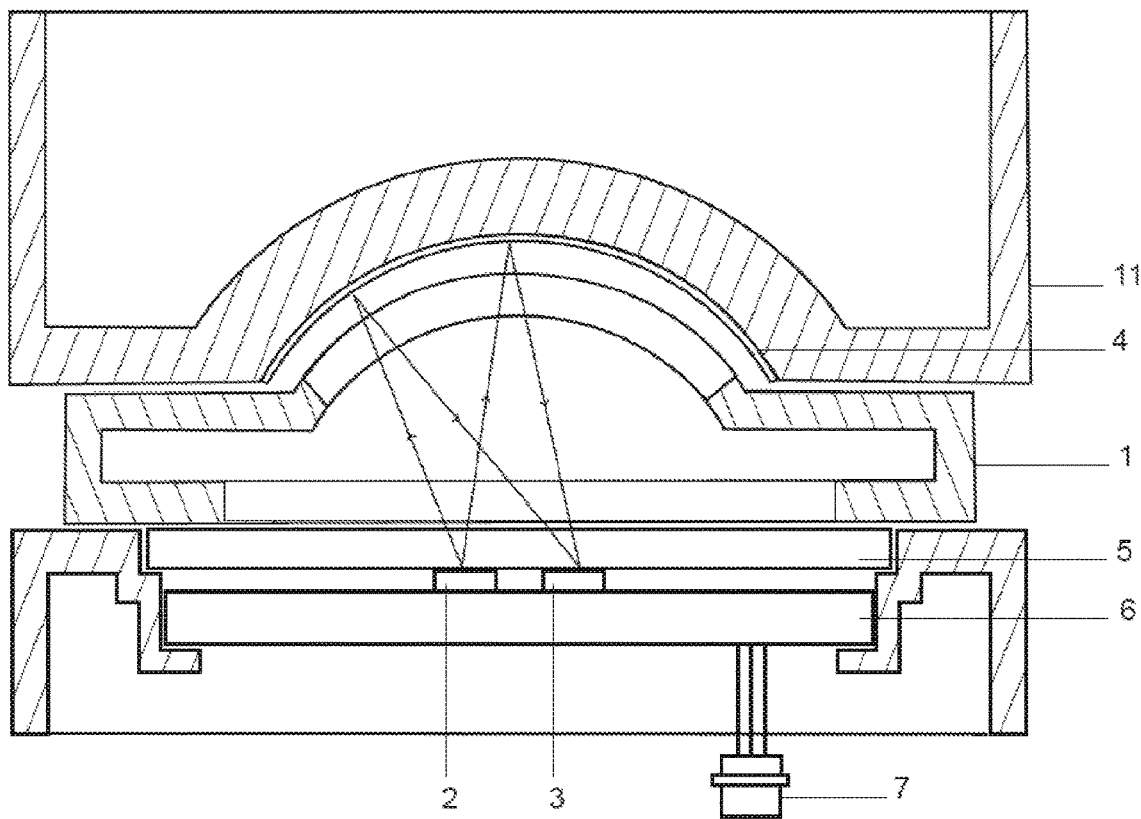
FIG. 5 shows a schematic illustration of a capnometer incorporating a disposable breath tube.

FIG. 5 shows a schematic of a capnometer incorporating a disposable breath tube (1). In this example, the capnometer comprises a body (11) of injection moulded high density polymer. The body (11) contains in some examples locating pins (not shown) which align to lugs in the printed circuit board (6). The reflector (4) is optionally integral to the body (11).

The emitter (2)/detector (3) pair are arranged on top of the printed circuit board (6). An electrical connector (7) is connected to the printed circuit board (6) in order to drive the emitter (2)/detector (3) pair.

In this example, an optical layer (5) comprising silicon is disposed on top of the emitter (2)/detector (3) pair.

A breath tube (1) is interspersed between the moulded body (11) and the printed circuit board (6). The breath tube (1) comprises windows or IR-transmissive or IR-transparent material. Therefore, the breath tube (1) in this example is disposable, allowing for a low-cost production of the breath tube (1).

Figure 6:
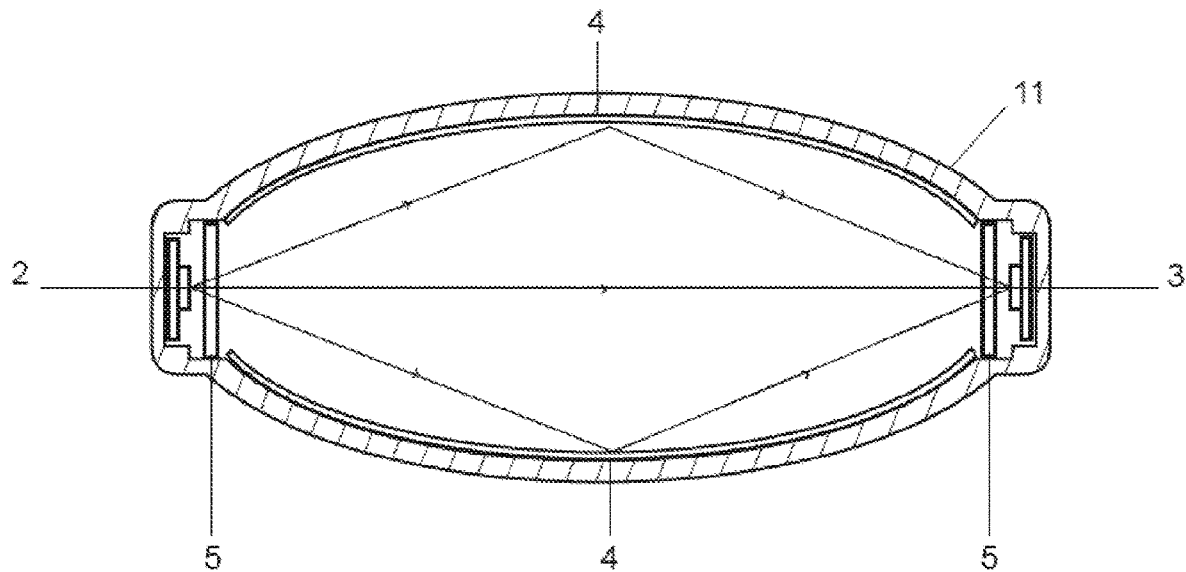
FIG. 6 shows a further schematic illustration of a capnometer.

FIG. 6 shows a schematic of a capnometer wherein the emitter (2) and detector (3) are arranged on opposite sides of the air flow region. This example exploits a reflecting geometry, wherein the emitter (2), the detector (3) and the reflector (4) are arranged such that IR light emitted by the emitter (2) passes through the air flow region via the reflector (4) to the detector (3).

In this configuration, the reflector (4) can be arranged on one side of the air flow region only, or, alternatively, on both sides of the air flow region as shown in FIG. 6.

Furthermore, the example of FIG. 6 allows using either a reflecting geometry, or a non-reflecting geometry in which IR light passes through the air flow region without being reflected by the reflector (4), or a combination of reflecting and non-reflecting geometries.

In this example, emitter (2) and detector (3) are mounted in a breath tube (not shown in FIG. 6), which is removable from the capnometer. Alternatively, emitter (2) and detector (3) can be mounted on two inner surfaces of the body (11) of the capnometer on opposing sides facing the air flow region. Emitter (2) and detector (3) are in some examples integral to the body (11) of the capnometer.

As shown in FIG. 6, optical layers (5) which, in some examples, comprise silicon, are arranged between the air flow region and the emitter (2) and the detector (3), respectively. It will be appreciated that only a single optical layer (5) may be arranged, either between the air flow region and the emitter (2), or between the air flow region and the detector (3). In this example, optical layers (5) are arranged between both the air flow region and the emitter (2) as well as the air flow region and the detector (3). As outlined above, (an) optical layer(s) (5) can improve a collection efficiency of IR light emitter by the emitter (2) onto the detector (3).

Figure 7:
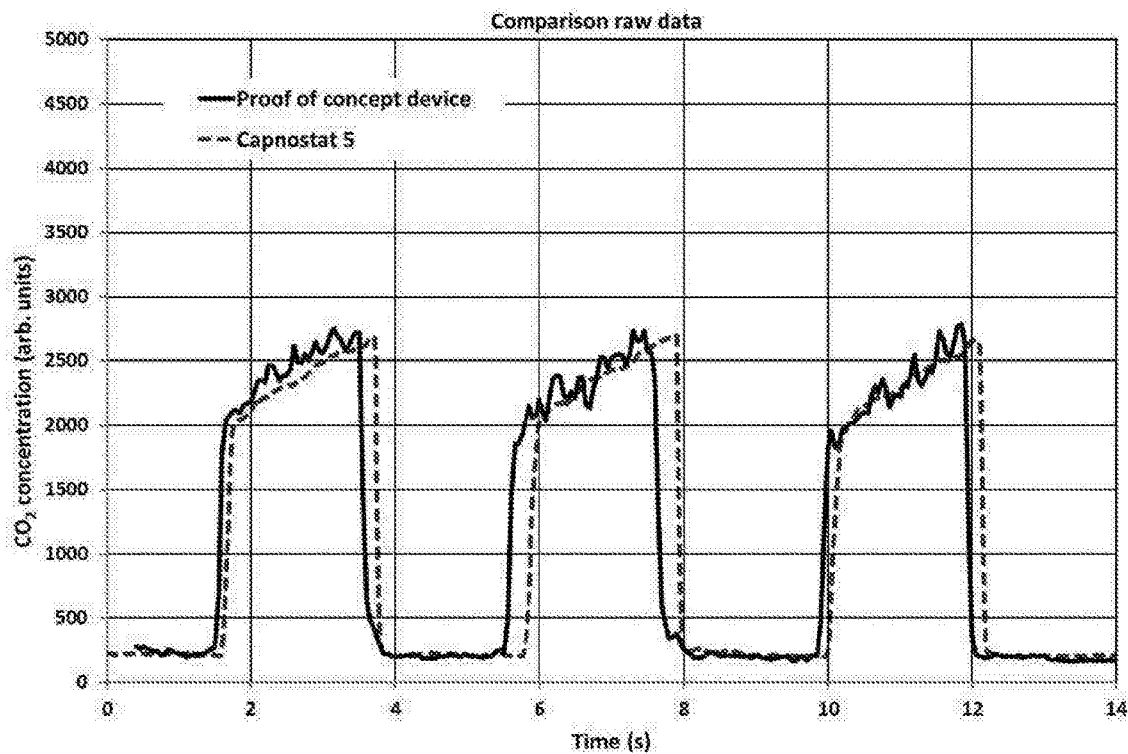
FIG. 7 shows $CO_2$ concentration as a function of time.

FIG. 7 shows measurements of $CO_2$ concentration as a function of time performed with a capnometer as described in embodiments herein, as well as with a standard Capnostat® 5 capnometer, respectively. In this example, three inspiration/expiration cycles of a patient have been recorded with each of the above-specified devices over a time period of 14 seconds.

It can be seen that measurements taken with the capnometer described herein show some minor fluctuations in the detected $CO_2$ concentration compared to the slightly more stable Capnostat® 5 capnometer. However, generally, the signals detected with each of the capnometers substantially coincide with regard to their frequency, amplitude, rise and fall time of a signal, and other characteristics. This example shows a proof of concept of the capnometer described in this specification.

As outlined above, one or more of a shape of the waveform, one or more peak heights of the waveform, an amplitude or amplitude variation of the waveform, a frequency composition of the waveform, a rise time of a $CO_2$ level, a slope of a $CO_2$ level versus time may be used to analyse a patient respiratory system function. Various conditions and/or diseases of the respiratory system, in particular the lung may be determined. These include, but are not limited to, bronchospasm, asthma, COPD, hypoventilation, hyperventilation, apnea, sedation, pulmonary embolism and others.

In some cases, there is a problem of contamination of the reflective surface and/or any IR-transmissive windows/components. Contamination may reduce the signal received by the detector (3) and it may appear as an increase in $CO_2$ level even if no change has actually occurred. One method to mitigate this is to monitor the inspiration phase of the breath cycle where fresh air with low $CO_2$ levels is passed through the sampling area. Typically, the $CO_2$ concentration is approximately 450 ppm. It will be appreciated that the threshold may vary and may preferably be adjusted depending on conditions of the area surrounding the device. If the measured $CO_2$ level is higher than the threshold, the system may indicate that the measurement is void. A correction to the measured $CO_2$ level can then be made.

In an alternative example, the capnometer comprises an additional emitter (2) which emits radiation centred around less or more than 4.26 μm, but still within the detecting range of the detector (3). The two emitters (2) may be pulsed in opposite phases so that the detector (3) detects the two emitters (2) at separate points in time. In this way, any scattering of radiation due to contamination may be similar between the two emitter radiations. A correction can then be applied to the signal from the emitter (2) emitting IR-light centred at or around 4.26 μm. It will be appreciated that alternatively or additionally, the signal detected by the detector (3) may be corrected based on the determined contamination.

In some cases, there is a problem of achieving accurate calibration of the system. This is particularly the case where a replaceable breath tube (1) is employed since there is a possibility of small variations in alignment. The device can be calibrated assuming the background $CO_2$ level is known. This might be the case if the air is ambient air. Alternatively, the $CO_2$ level can be obtained from a different information source.

Alternatively, a breath tube (1) incorporating a gas of known $CO_2$ level can be used for calibrating the device. The breath tube (1) comprises in some examples end caps which have removable elements such that after calibration, the removable elements can be peeled off and the device is ready to use.

Figure 8:
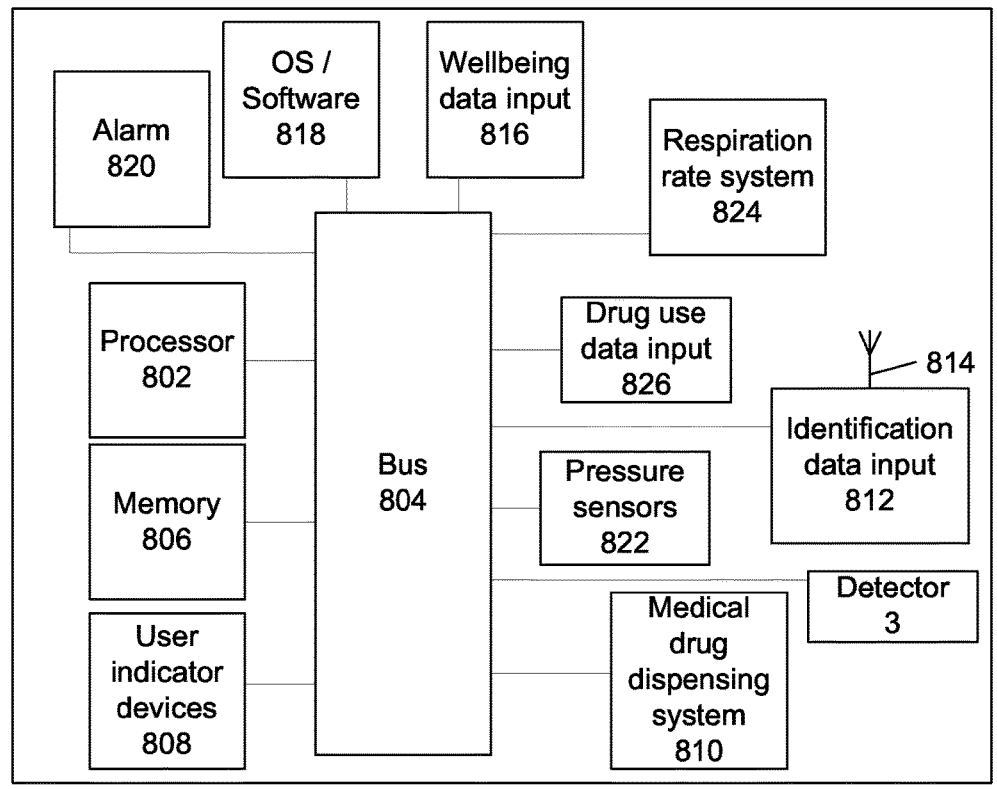
FIG. 8 shows a schematic illustration of components of a capnometer according to embodiments of the present invention.

FIG. 8 shows a schematic representation of a capnometer 800.

The capnometer 800 comprises a processor 802 which is configured to perform the various functions as outlined above, in particular, but not limited to the analysis of the signal from the detector 3 in order to provide $CO_2$ level data output.

The processor 802 is connected to the other units of the capnometer 800 via bus 804.

The capnometer further comprises an OS/software 818 which may be stored in an internal memory of the capnometer 800. The internal memory may be integral to memory 806.

The $CO_2$ level data output can be stored in memory 806 for later retrieval, for example for analysis by the patients GP or carer, and/or for making a comparison between a current $CO_2$ level data output and one or more previously obtained $CO_2$ level data outputs, as outlined above.

The capnometer 800 further comprises (one or more) user indicator devices 808. The user indicator devices 808 indicate a quality of the respiratory system function. The user indicator devices 808 are in this example further used to indicate one or more of a point time when a drug has been taken, a point in time when a drug should be taken, a type of drug which has been taken, a type of drug which should be taken, a dose which has been taken, a dose which should be taken, and whether a drug has been used up and/or has expired.

The capnometer 800 further comprises a medical drug dispensing system 810 which is used to control a release of a drug. The patient can control the release of the drug himself. Alternatively, the drug (type and/or dose and/or time) can be released automatically in response to one or more of the above indications which are determined using processor 802, and optionally indicated by the user indicator devices 808.

The capnometer 800 further comprises an identification data input 812 which is configured to receive identification data of the patient. As outlined above, identification data may be one or more of an identification code, fingerprint data, iris scan data, patient respiratory profile data, and other data. The identification data is received via data communications link 814. Alternatively, in other examples, the identification data is directly input into the identification data input 812.

As outlined above, the capnometer 800 may only be used when the identification data matches an identifier. The identifier is in this example stored in memory 806, or alternatively or additionally it can be stored external to the capnometer 800.

The capnometer 800 further comprises a wellbeing data input 816 which allows the patient to input wellbeing data which describes a health status of the patient. The processor 802 can then process the wellbeing data in combination with the signal from the detector 3 to determine whether, and to what extent, the drug has or has had an effect on the patient.

The capnometer 800 further comprises an alarm 820. The alarm is triggered if the patient does not take the drug (type of drug, and/or dose of drug, and/or time of taking the drug) according to a drug taking regime. The alarm can additionally or alternatively be sent to an external device or system, for example to alert the patient's GP or carer.

The capnometer 800 further comprises one or more pressure sensors 822 which are configured to measure a flow of $CO_2$ in the air flow region of the capnometer 800.

The capnometer 800 further comprises a respiration rate system 824 which is used to monitor a respiration rate of the patient and which outputs respiration rate data that can be processed by the processor 802.

The capnometer 800 further comprises a drug use data input 826 where the patient can enter data about their drug use. As outlined above, this information can be used to determine compliance with a drug taking regime, and depending on the compliance, the patient's GP or carer can be alerted.

Figure 9:
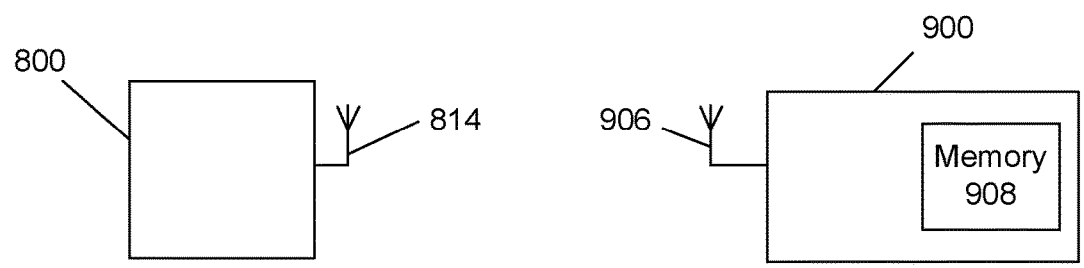
FIG. 9 shows a first example of a schematic illustration of a capnometer and an external device according to embodiments of the present invention.

FIG. 9 shows a schematic illustration of a capnometer 800 and an external device 900.

The external device 900 comprises a data communications link 906 which communicates with the data communications link 814 of the capnometer 800. The external device 900 comprises a memory 908 which stores a unique identifier code. This code can be sent by data communications link 906 to the capnometer 800 where it is received at data communications link 814. The code is then compared to an identifier stored in memory 806, and/or the code is used to unlock the capnometer 800 so that only a specific patient (or patients) can use the capnometer 800.

Memory 908 can be re-written manually, and/or it may automatically be re-written periodically.

Figure 10:
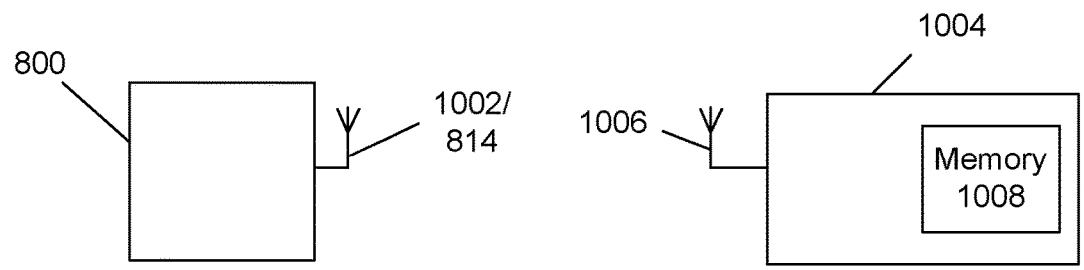
FIG. 10 shows a second example of a schematic illustration of a capnometer and an external monitoring system according to embodiments of the present invention.

FIG. 10 shows a schematic illustration of a capnometer 800 and a system 1004.

Data obtained via the capnometer 800 is processed by processor 802 and sent to system 1004 via the data communications link 1002. In this example, the data communications link 1002 and the above-specified data communications link 814 are the same, single data communications link.

The data can then be received at the system 1004 via data communications link 1006, and it can be stored in memory 1008.

The data may alternatively or additionally be stored internal to the capnometer 800, for example in memory 806. Memory 806 can then be accessed to obtain and analyse the data.

The data can be used by, for example, the patient's GP or carer for later analysis.

The data may be, but is not limited to, one or more of $CO_2$ level data, data obtained as outlined above via the user indicator devices 808, such as type, and/or dose, and/or time of dispensing a drug, $CO_2$ flow data, data obtained via the identification data input 812, respiration rate data, wellbeing data, data output via the alarm 820, and other data.

Memory 1008 can be re-written manually, and/or it may automatically be re-written periodically.

Figure 11:
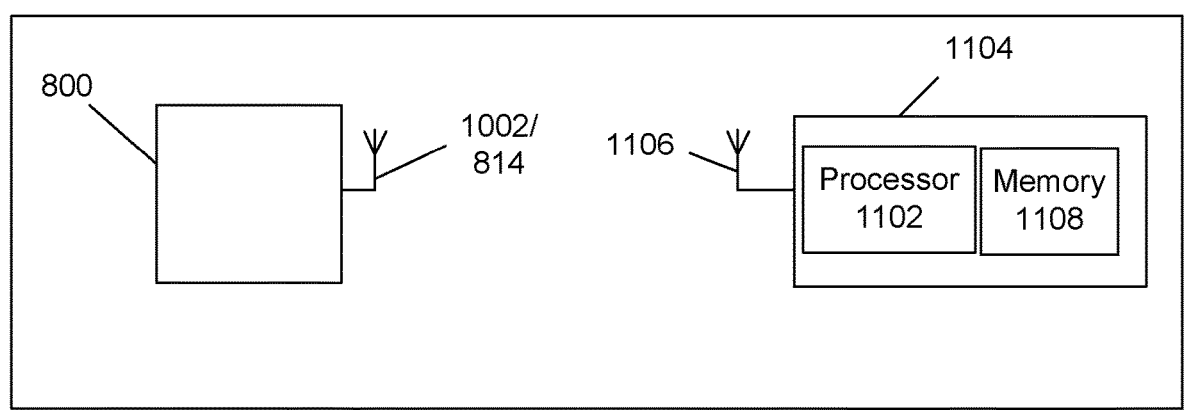
FIG. 11 shows a schematic illustration of a system according to embodiments of the present invention.

FIG. 11 shows a schematic of a system 1100 described herein.

The system 1100 comprises a capnometer 800 having a data communications link 814/1002 (or an inhaler 800 comprising the capnometer as described herein) and an analysis system 1104.

The analysis system 1104 comprises a processor 1102, a data communications link 1106 and a memory 1108.

The analysis system 1104 is in communication with the capnometer 800 via data communication links 814/1102 and 1106.

The memory 1108 of the analysis system 1104 stores patient data which is specific to one or more patients.

The analysis system 1104 is configured to modify an analysis algorithm used in the capnometer 800 based on an analysis of a $CO_2$ waveform by the signal processor of the capnometer 800; and/or to modify an indicator setting of an indicator of the capnometer 800 based on the analysis of the $CO_2$ waveform by the signal processor, wherein the indicator indicates a quality of the respiratory system function of the user of the capnometer, and/or to change a dose level of a drug dispensed using the capnometer based on the analysis of a $CO_2$ waveform by the signal processor. The analysis system 1104 is configured to transfer the modified analysis algorithm used to analyse the $CO_2$ waveform with the signal processor of the capnometer 800, and/or the modified indicator and/or changed dose level to the capnometer 800 for storage in the memory of the capnometer 800.

In this example, memory 1108 further stores patient data which is specific to further patients. The modification of the analysis algorithm and/or modification of the indicator setting and/or change of the dose level are dependent from the patient specific date of the further patients stored in memory 1108, which, as outlined above, is advantageous insofar that certain actions may be taken which are based on a previous analysis of $CO_2$ waveforms obtained from other patients which may indicate certain respiratory system function or malfunctions, in particular certain lung function or malfunctions.

The patient assessment can thereby be communicated by an indicator and/or display on the capnometer (or inhaler). Data transmission between the capnometer 800 and the analysis system 1104 (which can be a central database) occurs via a secure link.

The analysis system 1104 has access to additional computing power for performing higher-level data analysis (using processor 1102) on individual patient data combined with data from other patients.

This process will provide more detailed information on the patient respiratory condition to be used by medical practitioners. As outlined above, the modified routines can be securely transferred to the personal device.

Figure 12:
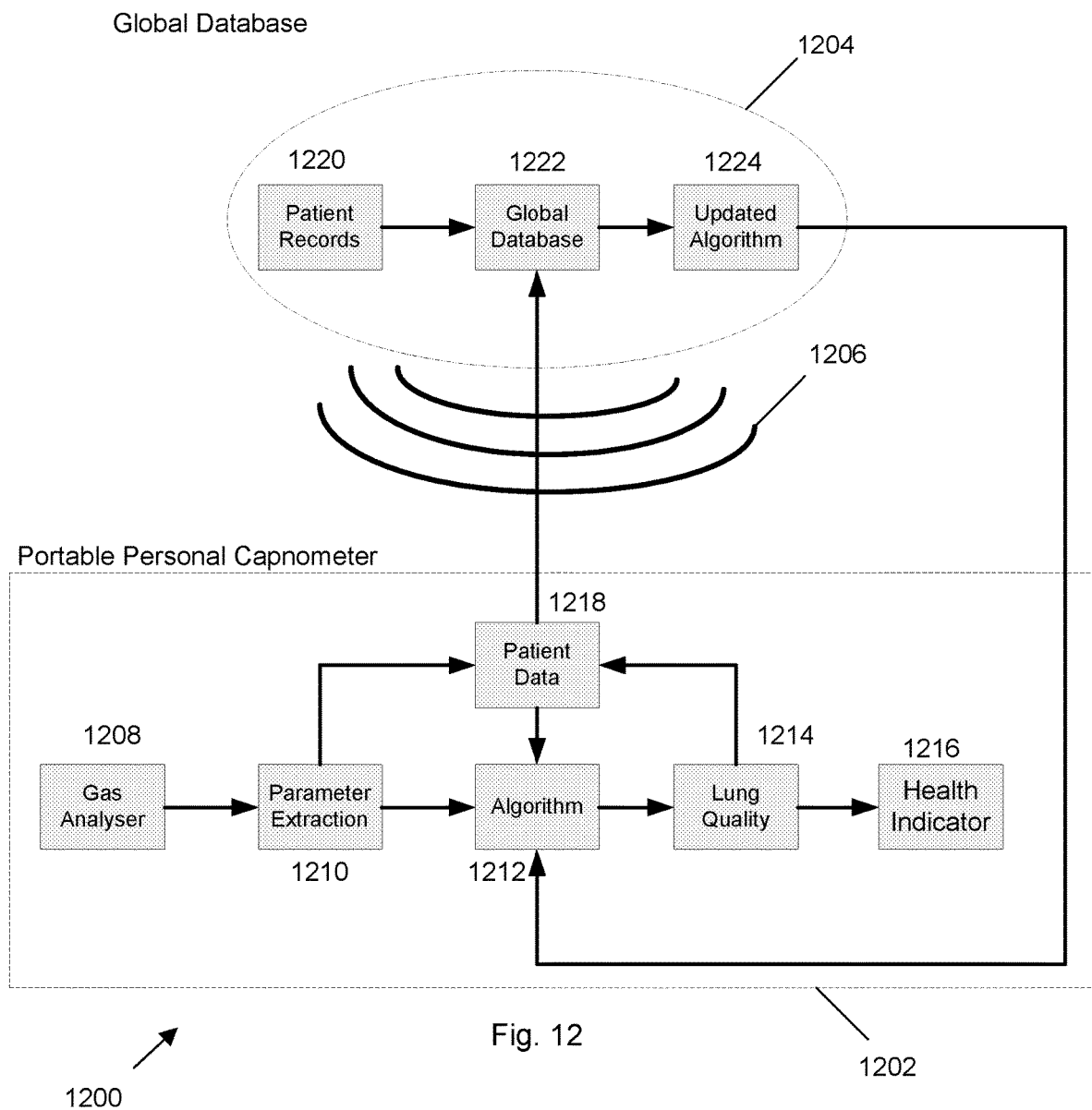
FIG. 12 shows a further schematic illustration of a system according to embodiments of the present invention.

FIG. 12 shows a schematic illustration of a system 1200 described herein.

The system 1200 comprises in this example a portable personal capnometer 1202. The capnometer 1202 is connected to a global database 1204 (for example a storage cloud or other storage system external to the capnometer 1202) via a wireless communication network 1206.

The capnometer 1202 comprises in this example a gas analyser 1208 which is in communication with a parameter extraction unit 1210. The gas analyser 1208 is configured to analyse a $CO_2$ waveform of air inhaled/exhaled by the user of the capnometer 1202. The parameter extraction unit 1210 is then used to extract parameters of the $CO_2$ waveform, in this example a shape of the waveform, one or more peak heights of the waveform, an amplitude of the waveform, an amplitude variation of the waveform, rise and fall time of a $CO_2$ level, a slope of the $CO_2$ level versus time and a frequency composition of the waveform.

The parameter extraction unit 1210 is in communication with the patient data unit 1218 and the algorithm unit 1212. The patient data unit 1218 receives patient data, inter alia, from the parameter extraction unit 1210. Parameters extracted by the parameter extraction unit 1210 are sent to the algorithm unit 1212 where the algorithm used to analyse patient respiratory system function, in particular lung function, can be modified, as outlined above.

The algorithm unit 1212 is in communication with the respiratory system quality unit 1214, which is a lung quality unit 1214 in this example, where the quality of a lung function of the user of the capnometer 1202 is determined.

Data obtained in the lung quality unit 1214 is communicated to the health indicator 1216 which is used to indicate the health status of the user of the capnometer 1202 based on the lung quality data obtained in the lung quality unit 1214.

In this example, data indicating the lung quality determined in the lung quality unit 1214 is communicated to the patient data unit 1218. Since the patient data unit 1218 is in this example coupled to the algorithm unit 1212, lung quality data can be communicated to the algorithm unit 1212 via patient data unit 1218 in order to modify the algorithm, if necessary. In some examples, the lung quality unit 1214 communicates directly with the algorithm unit 1212 to change the algorithm, if necessary.

The global database 1204 comprises in this example a memory 1220 storing patient records. The memory 1220 is coupled to a global database unit 1222 at which patient data from the patient data unit 1218 is received via the network 1206. The patient data from the patient data unit 1218 can be analysed in the global database unit 1222 and an updated algorithm is developed in the update algorithm unit 1224. In this example, the global database unit 1222 is also used to store patient data from (a) further patient(s).

The updated algorithm can be communicated from the update algorithm unit 1224 of the global database 1204 to the algorithm unit 1212 of the capnometer 1202, in this example via the same network 1206.

No doubt many other effective alternatives will occur to the skilled person. It will be understood that the invention is not limited to the described embodiments and encompasses modifications apparent to those skilled in the art and lying within the spirit and scope of the claims appended hereto.

The invention claimed is:

1. A capnometer for analyzing respiratory system function of a patient, the capnometer comprising:
   an air flow region through which air from said patient's respiratory system passes;
   an emitter configured to emit light, said emitter comprising a mid-IR semiconductor emitter configured to provide said emitted light at a wavelength in the range 3-5 µm;
   a reflector to reflect said emitted light;
   a detector to detect said emitted light, said detector comprising a mid-IR semiconductor detector;
   wherein said emitter and said detector are arranged such that light from said emitter passes through said air flow region to said detector;
   a memory to store patient data which is specific to said patient; and
   a signal processor coupled to said detector to analyze a $CO_2$ waveform representing a variation over time in a $CO_2$ level of air inhaled and/or exhaled by said patient,
   wherein one or more parameters of said respiratory system function are extracted from said patient data,
   wherein a comparison between said waveform and one or more of said waveforms which were obtained previously for said patient defines a metric with a baseline, wherein said comparing comprises monitoring a deviation of said waveform from said baseline, and wherein said metric is specific to a disease or type of disease of said patient,
   wherein said one or more parameters comprises rise and fall time of a $CO_2$ level,
   wherein said air flow region comprises one or more alignment pins incorporated into a breathing tube, and
   wherein said one or more alignment pins enable alignment of said reflector with said emitter and said detector.

2. A capnometer as claimed in claim 1, wherein said patient data comprises identification data of said patient.

3. A capnometer as claimed in claim 2, wherein said identification data comprises one or more of an identification code, fingerprint data, iris scan data and patient respiratory profile data.

4. A capnometer as claimed in claim 1, wherein said signal processor is configured to provide a $CO_2$ level data output defining said $CO_2$ waveform, and wherein said $CO_2$ level data output is stored in said memory or a second memory internal or external to said capnometer for later interrogation.

5. A capnometer as claimed in claim 4,
wherein said signal processor is further configured to use said $CO_2$ level data output to determine compliance data identifying episodes when a drug has or has not been taken by said patient, and to determine compliance with a drug taking regime from said compliance data, and
wherein said determination of said compliance with said drug taking regime comprises one or more of:
determining whether said patient uses said capnometer to obtain said $CO_2$ level data output;
determining, based on said waveform, whether said patient takes said drug;
determining whether said patient takes said drug based on drug use data provided by said patient at a drug use data input of said capnometer; and
determining whether said drug has been dispensed from said capnometer.

6. A capnometer as claimed in claim 1, wherein said signal processor is configured to analyze said respiratory system function responsive to one or more of: a shape of said waveform, one or more peak heights of said waveform, an amplitude or amplitude variation of said waveform, and a frequency composition of said waveform.

7. A capnometer as claimed in claim 1, further comprising one or more user indicator devices, wherein, based on said waveform, said user indicator devices indicate a quality of said respiratory system function.

8. A capnometer as claimed in claim 7, further comprising an alarm and/or messenger configured to be triggered dependent on said indication of said quality of said respiratory system function.

9. A capnometer as claimed in claim 7, wherein said processor is further configured to indicate when a therapeutic intervention is required based on said quality of said respiratory system function.

10. A capnometer as claimed in claim 1, wherein said signal processor is configured to determine from said waveform one or more of:
a first indication of a point in time when a drug has been taken;
a second indication of a point in time when a drug should be taken;
a third indication of a type of drug which has been taken;
a fourth indication of a type of drug which should be taken;
a fifth indication of a dose which has been taken;
a sixth indication of a dose which should be taken; and
a seventh indication that a drug has expired and/or has been used up.

11. A capnometer as claimed in claim 10, further comprising a medical drug dispensing system for controlling a release of a said drug responsive to a said determination, wherein said medical drug dispensing system is configured to automatically release a said drug and/or control a said type and/or dose and/or point in time of said release of a said drug.

12. A capnometer as claimed in claim 10, wherein said signal processor is further configured to determine when said drug should be released during a breath cycle.

13. A capnometer as claimed in claim 1, wherein said signal processor is further configured to determine, from changes in said waveform over time during a single use of said capnometer by said patient, a variation in a condition of said respiratory system function.

14. A capnometer as claimed in claim 1, further comprising a wellbeing data input for allowing said patient to input wellbeing data, said wellbeing data describing a health status of said patient, wherein said processor is further configured to process said wellbeing data in combination with a detector signal to determine an effect of a drug on said patient.

15. A capnometer as claimed in claim 1, wherein the capnometer is configured to be part of an inhaler.

16. A system comprising:
the capnometer of claim 1 or the capnometer of claim 15; and
an analysis system in communication with said capnometer,
wherein said analysis system comprises an analysis system memory to store said patient data; and
wherein said analysis system is configured to:
i) modify an indicator setting of an indicator of said capnometer, wherein said indicator indicates a quality of said respiratory system function; and/or
ii) change a dose level of a drug dispensed using said capnometer;
wherein said analysis system is further configured to transfer said modified indicator setting and/or changed dose level to said capnometer for storage in the memory of said capnometer, wherein data stored in said memory of said analysis system further comprises patient data specific to further patients, and wherein said modification of said indicator setting and/or change of said dose level are further dependent from said patient data specific to said further patients.

17. A method of monitoring patient compliance with a drug-taking regime, the method comprising:
monitoring $CO_2$ levels in exhaled breath of the patient with a capnometer as claimed in claim 1;
storing data from said monitoring;
using said stored data to determine compliance data identifying episodes when said drug has or has not been taken; and
determining compliance with said drug taking regime from said compliance data, and wherein said compliance data further identifies a dose which has been taken.

18. The capnometer of claim 1, wherein said deviation of said waveform from said baseline is used to determine an indication selected from the group consisting of: a point in time when a drug has been taken, a point in time when a drug should be taken, a type of drug which has been taken, a type of drug which should be taken, a dose which has been taken, a dose which should be taken, a drug that has expired and/or been used up, and combinations thereof.

19. The capnometer of claim 1, wherein said comparison is specific to said patient, and based on one or more variables specific to said patient.

20. The capnometer of claim 1, wherein said air flow region comprises a mid-IR transmissive portion aligned with said emitter and said detector to allow mid-IR light to pass through said transmissive portion into, and out of, said air flow region, and
wherein said mid-IR transmissive portion comprises a coating that increases an efficiency of collection of said emitted light on to said detector.

21. The capnometer of claim 20, wherein said mid-IR transmissive portion comprises a separate window.

22. A capnometer for analyzing respiratory system function of a patient, the capnometer comprising:
an air flow region through which air from said patient's respiratory system passes;
an emitter configured to emit light, said emitter comprising a mid-IR semiconductor emitter configured to provide said emitted light at a wavelength in the range 3-5 µm;
a detector to detect said emitted light, said detector comprising a mid-IR semiconductor detector;
wherein said emitter and said detector are arranged such that light from said emitter passes through said air flow region to said detector;
a memory to store patient data which is specific to said patient; and
a signal processor coupled to said detector, said signal processor configured to analyze said respiratory system function responsive to one or more parameters of a $CO_2$ waveform that represents a variation over time in a $CO_2$ level of air inhaled and/or exhaled by said patient,
wherein said one or more parameters is selected from the group consisting of: a shape of said waveform, one or more peak heights of said waveform, an amplitude or amplitude variation of said waveform, a frequency composition of said waveform, and combinations thereof,
wherein a comparison between said waveform and one or more of said waveforms which were obtained previously for said patient defines a metric with a baseline, wherein said comparing comprises monitoring a deviation of said waveform from said baseline, and wherein said metric is specific to a disease or type of disease of said patient,
wherein said signal processor is further configured to:
(i) determine from said waveform one or more of:
a first indication of a point in time when a drug has been taken;
a second indication of a point in time when a drug should be taken;
a third indication of a type of drug which has been taken;
a fourth indication of a type of drug which should be taken;
a fifth indication of a dose which has been taken;
a sixth indication of a dose which should be taken; and
a seventh indication that a drug has expired and/or has been used up, and
(ii) determine, from changes in said waveform over time during a single use of said capnometer by said patient, a variation in a condition of said respiratory system function,
wherein said air flow region comprises one or more alignment pins incorporated into a breathing tube, wherein said one or more alignment pins enable alignment of a reflector with said emitter and said detector.

23. The capnometer of claim 22, further comprising:
a medical drug dispensing system for controlling a release of a said drug responsive to a said determination,
wherein said medical drug dispensing system is configured to automatically release a said drug and/or control a said type and/or dose and/or point in time of said release of a said drug,
wherein said signal processor is further configured to:
(i) determine when said drug should be released during a breath cycle, and
(ii) determine compliance data identifying episodes when a drug has or has not been taken by said patient, and to determine compliance with a drug taking regime from said compliance data, and wherein said determination of said compliance with said drug taking regime comprises one or more of:
determining whether said patient uses said capnometer to obtain said CO2 level data output;
determining, based on said waveform, whether said patient takes said drug;
determining whether said patient takes said drug based on drug use data provided by said patient at a drug use data input of said capnometer; and
determining whether said drug has been dispensed from said capnometer.

24. A capnometer for analyzing respiratory system function of a patient, the capnometer comprising:
an air flow region through which air from said patient's respiratory system passes;
an emitter configured to emit light, said emitter comprising a mid-IR semiconductor emitter configured to provide said emitted light at a wavelength in the range 3-5 µm;
a detector to detect said emitted light, said detector comprising a mid-IR semiconductor detector;
wherein said emitter and said detector are arranged such that light from said emitter passes through said air flow region to said detector;
a plurality of additional emitters, wherein each of said plurality of additional emitters emits light at a different respective wavelength, wherein each of the different respective wavelengths is within a detection range of said detector, and wherein, during an inspiration and/or an expiration of said patient, said plurality of additional emitters pulse such that said light from each of said plurality of additional emitters is detected by said detector at a different respective point in time;
a memory to store patient data which is specific to said patient;
a signal processor coupled to said detector to analyze a $CO_2$ waveform representing a variation over time in a $CO_2$ level of air inhaled and/or exhaled by said patient;
wherein a comparison between said waveform and one or more of said waveforms which were obtained previously for said patient defines a metric with a baseline,
wherein parameters of said respiratory system function are extracted from said waveform, said parameters comprising: a shape of said waveform, one or more peak heights of said waveform, an amplitude of said waveform, an amplitude variation of said waveform, rise and fall time of a $CO_2$ level, a slope of said $CO_2$ level versus time, and a frequency composition of said waveform,
wherein said signal processor determines that a measurement of said inspiration and/or said expiration of said patient is void when a scattering of light emitted by said plurality of additional emitters correlates between at least two emitters in said plurality of additional emitters at one of the different respective points in time, and
wherein said signal processor corrects a signal from said detector when said measurement is void.

* * * * *